United States Patent
Meza-Romero et al.

(10) Patent No.: US 11,945,855 B2
(45) Date of Patent: Apr. 2, 2024

(54) RECOMBINANT POLYPEPTIDES COMPRISING MODIFIED MHC CLASS II DRA1 DOMAINS AND METHODS OF USE

(71) Applicants: Oregon Health & Science University, Portland, OR (US); The United States Government as represented by the Department of Veterans Affairs, Washington, DC (US)

(72) Inventors: Roberto Meza-Romero, Beaverton, OR (US); Arthur A. Vandenbark, Portland, OR (US); Halina Offner, Portland, OR (US)

(73) Assignees: Oregon Health & Science University, Portland, OR (US); The United States Government as represented by the Department of Veterans Affairs, Washington, DC (US)

( * ) Notice: Subject to any disclaimer, the term of this patent is extended or adjusted under 35 U.S.C. 154(b) by 550 days.

(21) Appl. No.: 17/282,455

(22) PCT Filed: Oct. 4, 2019

(86) PCT No.: PCT/US2019/054850
§ 371 (c)(1),
(2) Date: Apr. 2, 2021

(87) PCT Pub. No.: WO2020/072992
PCT Pub. Date: Apr. 9, 2020

(65) Prior Publication Data
US 2021/0380660 A1    Dec. 9, 2021

Related U.S. Application Data

(60) Provisional application No. 62/741,941, filed on Oct. 5, 2018.

(51) Int. Cl.
*C07K 14/74*       (2006.01)
*A61K 39/00*       (2006.01)
*A61P 37/06*       (2006.01)

(52) U.S. Cl.
CPC .... *C07K 14/70539* (2013.01); *A61K 39/0008* (2013.01); *A61P 37/06* (2018.01); *A61K 2039/6031* (2013.01)

(58) Field of Classification Search
CPC ........ A61K 2039/6031; A61K 39/0008; A61P 37/06; C17K 14/70539
See application file for complete search history.

(56) References Cited

U.S. PATENT DOCUMENTS

| | | |
|---|---|---|
| 2014/0079701 A1 | 3/2014 | Miller et al. |
| 2015/0044245 A1 | 2/2015 | Vandenbark et al. |
| 2015/0098956 A1 | 4/2015 | Vandenbark et al. |
| 2015/0099706 A1 | 4/2015 | Offner-Vandenbark et al. |
| 2017/0114117 A1 | 4/2017 | Vandenbark et al. |
| 2017/0369577 A1 | 12/2017 | Meza-Romero et al. |
| 2018/0271935 A1 | 9/2018 | Offner et al. |

FOREIGN PATENT DOCUMENTS

| | | |
|---|---|---|
| CN | 104105503 A | 10/2014 |
| JP | 2015-505315 | 2/2015 |
| WO | WO 2005/044982 | 5/2005 |
| WO | WO 2018/087597 A1 | 5/2018 |

OTHER PUBLICATIONS

Benedek et al., "HLA-DRα1-mMOG-35-55 treatment of experimental autoimmune encephalomyelitis reduces CNS inflammation, enhances M2 macrophage frequency, and promotes neuroprotection," *J. Neuroinflammation*, 12:123, 2015.

Meza-Romero et al., "Increased CD74 binding and EAE treatment efficacy of a modified DRα1 molecular construct," *Metab Brain Dis*, vol. 34, No. 1, pp. 153-164, 2019 (Author manuscript version, 22 pages).

Meza-Romero et al., "HLA-DRα1 constructs block CD74 expression and MIF effects in experimental autoimmune encephalomyelitis," *J Immunol*, vol. 192, No. 9, pp. 4164-4173, 2014 (Author manuscript version, 25 pages).

Huan et al., "Rationally designed mutations convert complexes of human recombinant T cell receptor ligands into monomers that retain biological activity," *Journal of Chemical Technology and Biotechnology*, vol. 80, No. 1, pp. 2-12, 2005.

*Primary Examiner* — Bao Q Li
(74) *Attorney, Agent, or Firm* — Klarquist Sparkman, LLP

(57) ABSTRACT

Recombinant polypeptides comprising a modified DRα1 domain are provided. In some embodiments, the polypeptides include the modified DRα1 domain, an antigenic peptide, and optionally a linker sequence. Pharmaceutical compositions comprising the recombinant polypeptides, methods of treating inflammatory disease using said recombinant polypeptides or pharmaceutical compositions, and expression constructs comprising nucleic acids that encode the recombinant polypeptides are also provided.

20 Claims, 11 Drawing Sheets
Specification includes a Sequence Listing.

FIG. 1

```
              10         20         30         40         50         60
DM1  WPDDLQNHTF LHTV-YCQDG SPSVGLSEAY DEDQLFFFDF SQNTRVPRLP EFADWAQEQG
DO1  AGATKADHMG SYGPAFYQSY GASGQFTHEF DEEQLFSVDL KKSEAVWRLP EFGDFARFDP
DQ1  GEDIVADHVA SCGVNLYQFY GPSGQYTHEF DGDEQFYVDL ERKETAWRWP EFSKFGGFDP
DQ2  GEDIVADHVA SYGVNFYQSH GPSGQYTHEF DGDEEFYVDL ETKETVWQLP MFSKFISFDP
DP4  RRVIKADHVS TYAA-FVQTH RPTGEFMFEF DEDEMFYVDL DKKETVWHLE EFGQAFSFEA
DP2  AGAIKADHVS TYAA-FVQTH RPTGEFMFEF DEDEMFYVDL DKKETVWHLE EFGQAFSFEA
DR1  SWAIKEEHVI IQA-EFYLNP DQSGEFMFDF DGDEIFHVDM AKKETVWRLE EFGRFASFEA
IAk  EDDIEADHVG SYGITVYQSP GDIGQYTFEF DGDELFYVDL DKKETVWMLP EFAQLRRFEP
IAd  EDDIEADHVG FYGTTVYQSP GDIGQYTHEF DGDELFYVDL DKKKTVWRLP EFGQLILFEP
IAb  EDDIEADHVG TYGTSVYQSP GDIGQYTFEF DGDELFYVDL DKKKTVWRLP EFGQLASFDP
IAf  EDDIEADHVG FYGISVYQSP GDIGQYTFEF DGDEWFYVDL DKKETVWRLP EFGQLTSFDP
IAu  EDDIEADHVG SYGIVVYQSP GDIGQYTFEF DGDELFYVDL DKKETIWMLP EFAQLRSFDP
IAq  EDDIEADHVG SYGIVVYQSP GDIGQYTHEF DGDEWFYVDL DKKETVWMLP EFGQLTSFDP
```

FIG. 4A

```
MGIKEEHVIIQAEFYLNPDQSGEFMFDFDGDEIFHVDMAKKETVWRLEEFGRFASFEAQGALANIAVDKANLEIMTKRSNYTPITN

MGIKEEHVIIQAEFYLNPDQSGEFMFDFDG                                                      P1
         QAEFYLNPDQSGEFMFDFDGDEIFHVDMAK                                             P2
                 SGEFMFDFDGDEIFHVDMAKKETVWRLEEF                                     P3
                        DEIFHVDMAKKETVWRLEEFGRFASFEAQG                              P4
                                KETVWRLEEFGRFASFEAQGALANIAVDKA                      P5
                                       GRFASFEAQGALANIAVDKANLEIMTKRSN               P6
                                              ANIAVDKANLEIMTKRSNYTPTIN              P7
```

FIG. 4B

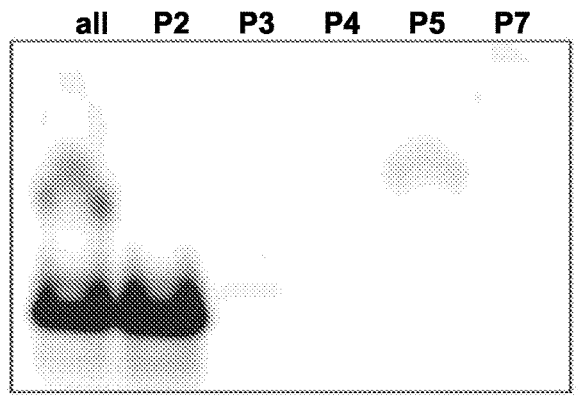

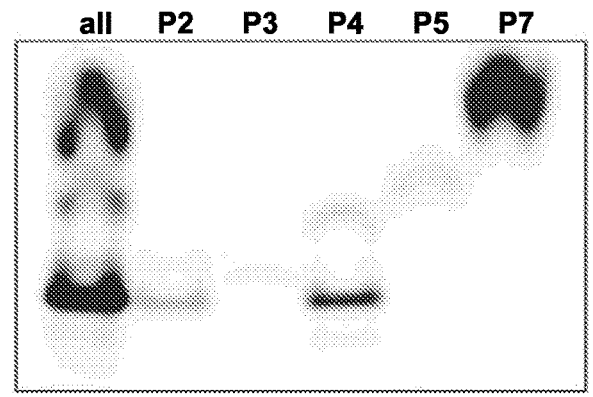

H2M

FIG. 7A
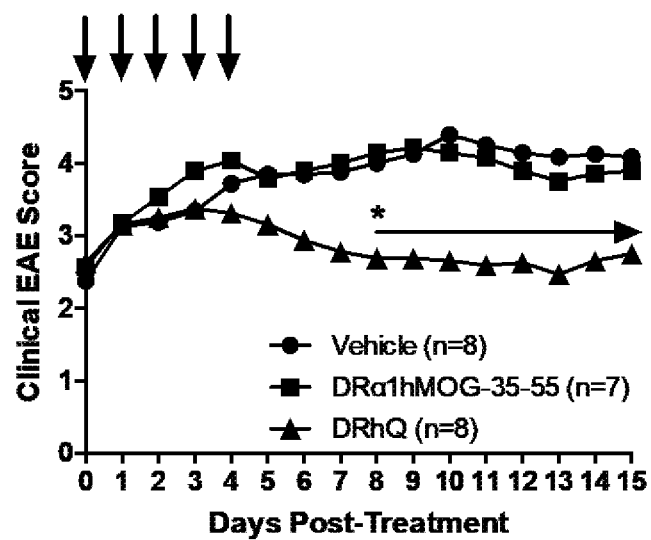
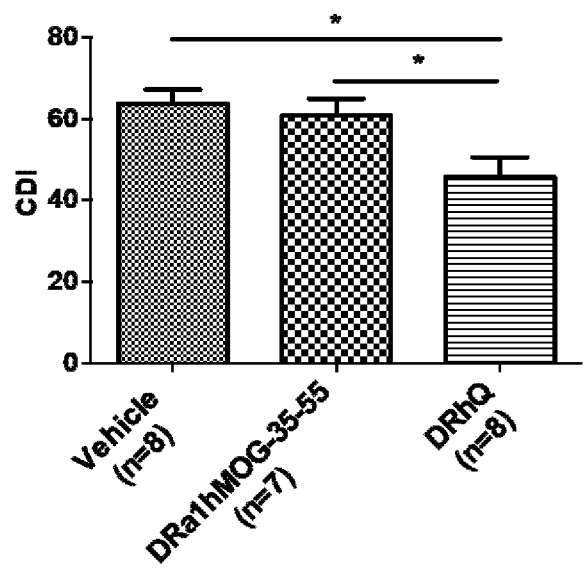

FIG. 7B
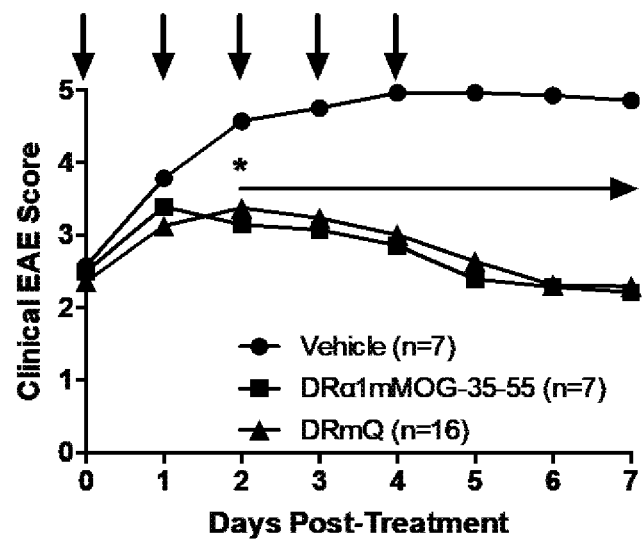
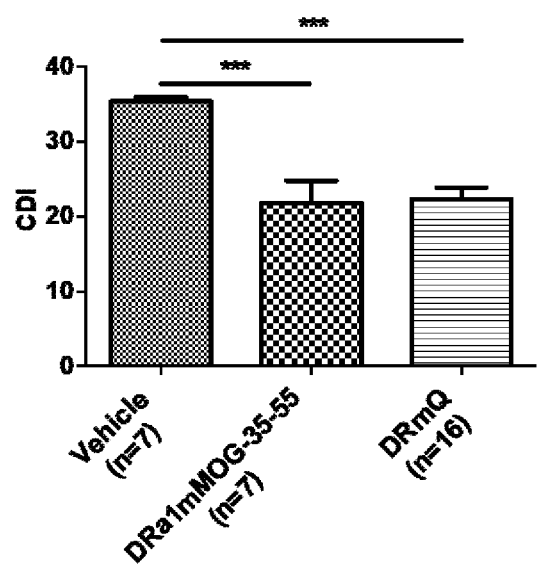

RECOMBINANT POLYPEPTIDES COMPRISING MODIFIED MHC CLASS II DRA1 DOMAINS AND METHODS OF USE

CROSS REFERENCE TO RELATED APPLICATIONS

This application is the § 371 U.S. National Stage of International Application No. PCT/US2019/054850, filed Oct. 4, 2019, which was published in English under PCT Article 21(2), which in turn claims the benefit of U.S. Provisional Application No. 62/741,941, filed Oct. 5, 2018, which is incorporated herein by reference in its entirety.

ACKNOWLEDGMENT OF GOVERNMENT SUPPORT

This invention was made with government support under AI122574 awarded by The National Institutes of Health. The government has certain rights in the invention.

FIELD

This disclosure relates to recombinant therapeutic proteins, particularly modified partial MHC molecules, and their use in the treatment of inflammatory disease.

BACKGROUND

Multiple sclerosis (MS) is the most prevalent chronic inflammatory disease of both white and grey matter of the central nervous system, affecting more than 2 million people worldwide and at least 400,000 in the United States (GBD 2015 Neurological Disorders Collaborator Group, *Lancet Neurol.* 16:877-897, 2017). The inflammatory process in MS is mediated by autoimmune driven demyelination, often accompanied by neurodegenerative injuries. Currently there is no cure for MS. Thus, MS patients have to rely on disease modifying therapies in order to ameliorate some of the disease signs (Wingerchuk et al., *Mayo Clin. Proc.* 89:225-240, 2014). About 15 disease modifying medications are available for the relapsing and remitting form of MS (Reich et al., *N. Engl. J. Med.* 378:169-180, 2018). However, there is a continuing need for improved therapies for MS.

SUMMARY

Disclosed herein are modified major histocompatibility (MHC) class II DRα1 polypeptides. These modified DRα1 polypeptides exhibit altered affinity for CD74 and ability to compete with macrophage migration inhibitory factor (MIF) for binding to CD74, without apparent effects on the structure of the molecule.

In some embodiments, disclosed are recombinant polypeptides that include a MHC class II DRα1 domain including a glutamine residue at a position corresponding to amino acid position 14 of SEQ ID NO: 1 (referred to as L14Q mutation in some instances or as L50Q when in the context of DRα1-MOG-35-55 constructs). The glutamine residue replaces the native leucine residue at this position (FIG. 1). In some examples, the DRα1 domain is a human DRα1 domain. The sequence of the recombinant DRα1 domain includes or consists of the amino acid sequence of SEQ ID NO: 1, in some examples.

In other embodiments, disclosed are recombinant polypeptides that include a DRα1 domain including a glutamine residue at a position corresponding to amino acid position 14 of SEQ ID NO: 1, an antigenic peptide, and optionally a linker sequence. In one example, the linker sequence includes a first glycine-serine spacer, a thrombin cleavage site and a second glycine-serine spacer. The antigenic peptide may be a myelin oligodendrocyte glycoprotein (MOG) polypeptide, such as human or mouse MOG-35-55. In some embodiments, the sequence of the recombinant polypeptide includes or consists of the amino acid sequence of SEQ ID NO: 2 or SEQ ID NO: 3.

Also provided are nucleic acid molecules encoding the recombinant polypeptides disclosed herein. Exemplary nucleic acid molecules include SEQ ID NOs: 4-6. In some embodiments, the nucleic acid is included in an expression construct and/or a vector. Also disclosed are cells or cell lines that include the expression construct or vector.

In some embodiments the disclosed recombinant polypeptides or nucleic acids encoding the recombinant polypeptides are included in a pharmaceutical composition, for example, with a pharmaceutically acceptable carrier. In some examples, the composition includes at least 5 mg/kg of the recombinant polypeptide.

Further disclosed herein are methods of treating inflammatory disorders that include administering a disclosed recombinant polypeptide or pharmaceutical composition (such as a composition including the polypeptide of any one of SEQ ID NOs: 1-3) to a subject that is suffering from the inflammatory disorder. In some examples, the subject has multiple sclerosis (or its mouse model, EAE).

The foregoing and other features of the disclosure will become more apparent from the following detailed description, which proceeds with reference to the accompanying figures.

BRIEF DESCRIPTION OF THE DRAWINGS

FIG. 1 is an amino acid sequence alignment showing the residue at position 18 (Q18, arrow) of HLA Class II α1 domains (SEQ ID NOs: 7-19). This residue is conserved among most of the human and mouse Class II α1 domains, including those from non-antigen presenting DM and DO regulatory molecules. DRα1, however, has a leucine (L) at this position. This residue is shown as position 18 in this alignment; however, in the crystal structure, this residue is located at position 14.

FIG. 2B is an alignment showing the partial amino acid sequence of the DRα1 mutants compared to the wild type versions. In addition to the DRα1-hMOG-35-55 (DRα1 with human MOG-35-55 peptide; SEQ ID NO: 20) and the DRhQ (DRα1-hMOG-35-55 with glutamine substitution; SEQ ID NO: 21), the DRα1-mMOG-35-55 (DRα1 with mouse MOG-35-55 peptide; SEQ ID NO: 22) and DRmQ (DRα1-mMOG-35-55 with glutamine substitution; SEQ ID NO: 23) were synthesized. The arrow indicates the positions of the mutagenesis. DRα1-hMOG and DRα1-mMOG also differ at position 9 (P for S).

Figure 3A:
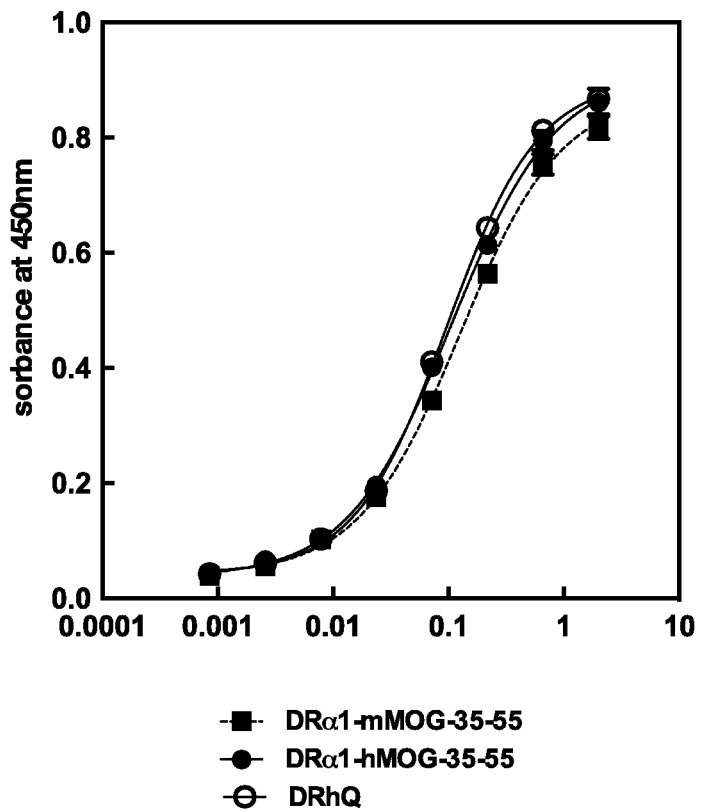
Figure 3B:
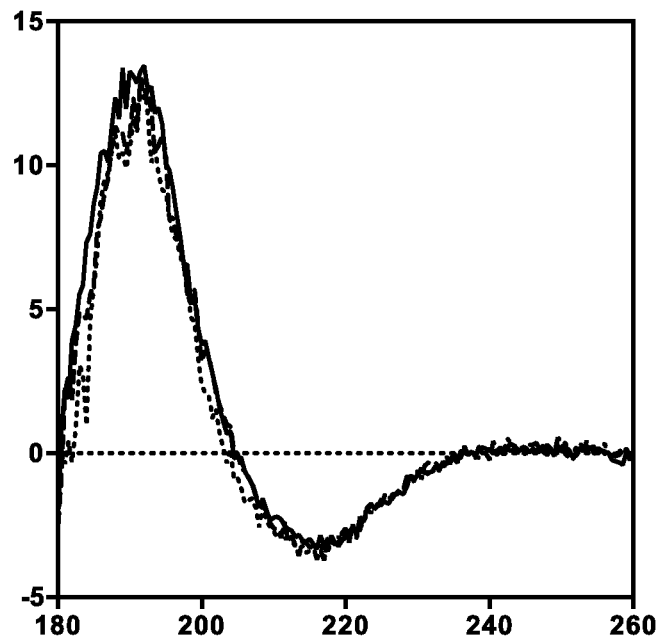

FIGS. 3A and 3B are graphs showing DRα1-derived constructs DRα1-hMOG-35-55, DRα1-mMOG-35-55 and DRhQ were probed with the Fab G4 in order to evaluate immunological differences between the DRα1-hMOG-35-55, DRhQ and DRα1-mMOG-35-55 (FIG. 3A). Circular dichroism was used to evaluate differences in secondary structure content (FIG. 3B).

FIGS. 4A-4C show the strategy designed to locate the DRα1 binding site for CD74. FIG. 4A is a schematic showing overlapping peptides (full length (SEQ ID NO: 24) and P1-P7, SEQ ID NOs: 25-31, respectively) used to narrow down the region(s) binding to CD74. Mouse CD74 (FIG. 4B) or mouse H2M (FIG. 4C) were immunoprecipitated with specific monoclonal antibodies adsorbed to Protein A/G beads and then a pool of the overlapping peptides ("all") or individual peptides were added. Immune complexes were washed extensively and bound peptides were eluted with electrophoresis sample buffer containing 1% SDS. Eluted material was analyzed by electrophoresis by SDS-peptide gels in Tris-Tricine. Gels were then scanned for the fluorophore in a BioRad Molecular Imager FX.

Figure 5A:
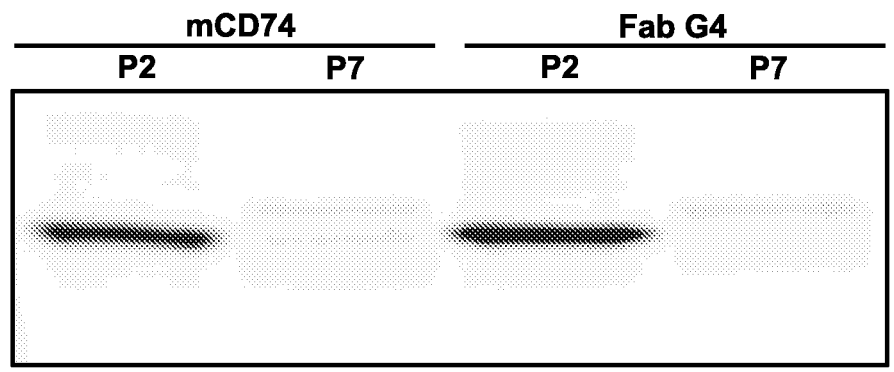
Figure 5B:
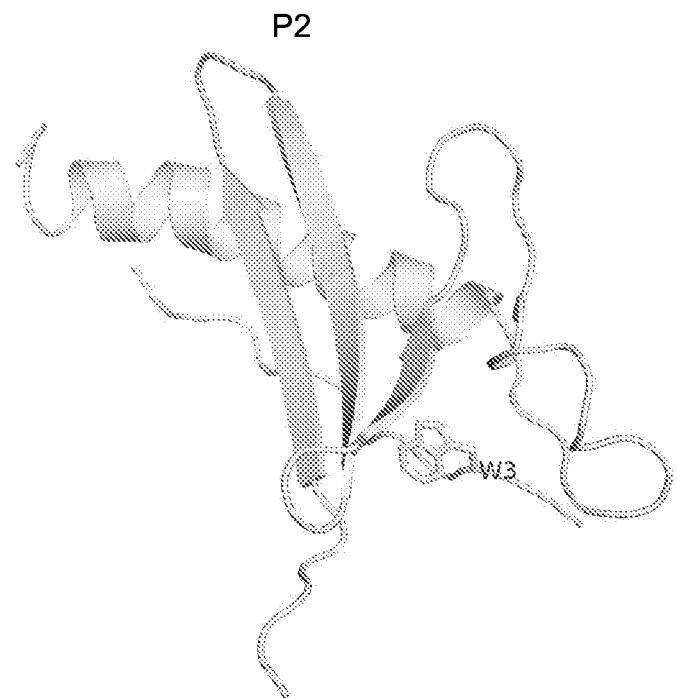
Figure 5C:
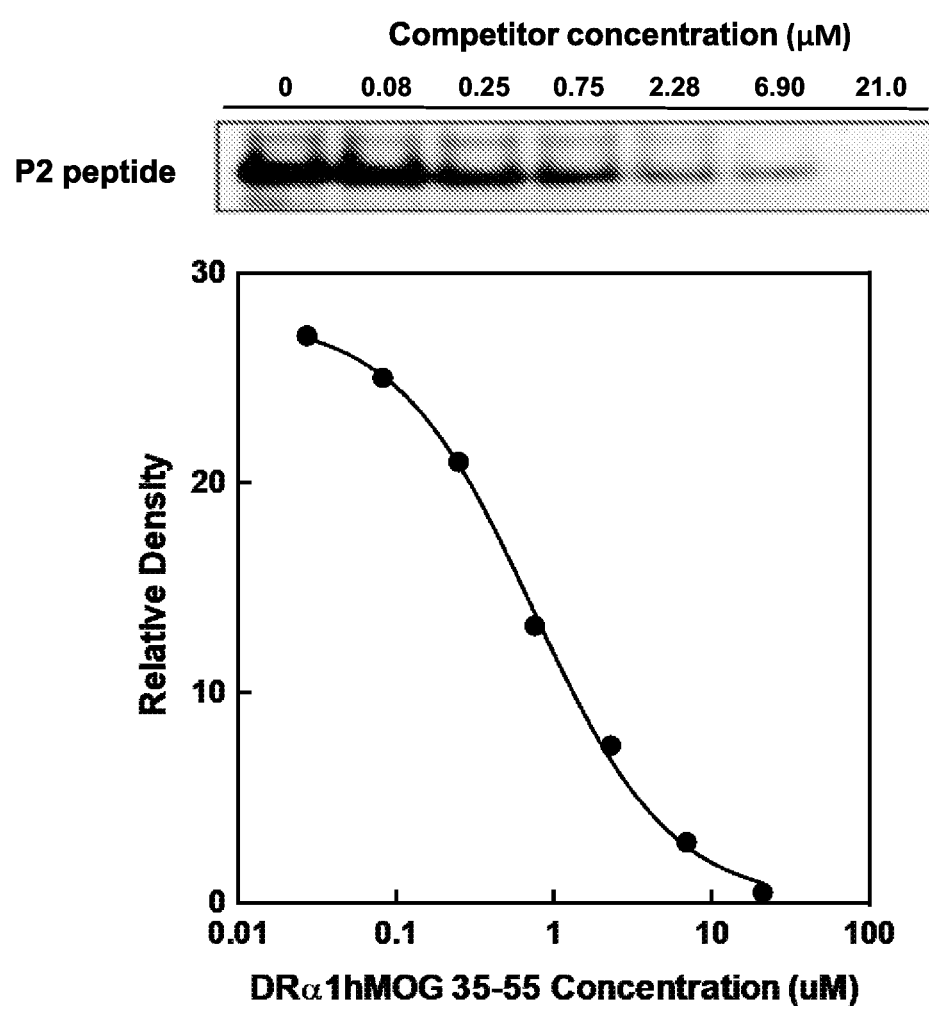

FIGS. 5A-5C are a series of panels showing binding of P2 or P7 peptides to CD74 or Fab G5. Peptides P2 and P7 were tested individually for their ability to bind immunoprecipitated mouse CD74 or FabG4 adsorbed to Protein A/G beads and Protein L beads, respectively (FIG. 5A). Only P2 was able to bind CD74 and Fab G4. P7 was unable to bind to any of the targets. The location of the P2 peptide in the DRα1-hMOG-35-55 polypeptide is shown in FIG. 5B. Competition experiment showed that DRα1-hMOG-35-55 was able to outcompete the binding of the FITC-labeled P2 peptide to immunoprecipitated CD74 with a relative affinity ($K_D$) of 750 nM (FIG. 5C).

Figure 6A:
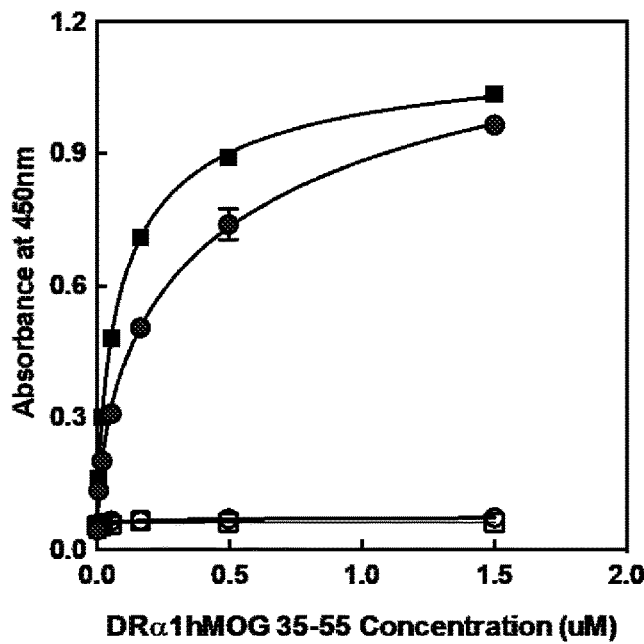
Figure 6B:
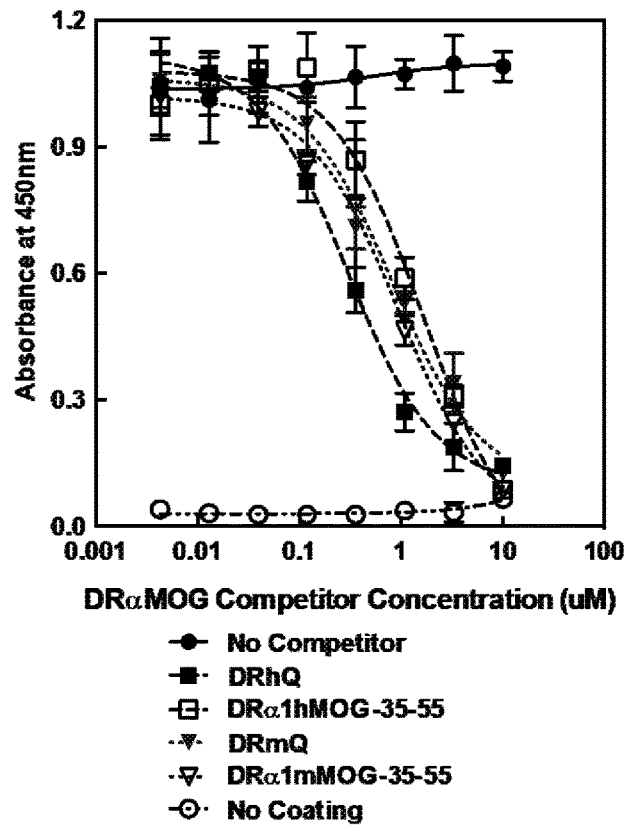

FIGS. 6A and 6B are graphs showing binding of constructs to rhCD74. Constructs DRα1-hMOG-35-55 and DRhQ were assessed for direct binding to rhCD74 onto ELISA plates by direct binding assay with or without G4 Fab during the binding (FIG. 6A). The $K_D$ calculated polypeptides were 0.65 µM for DRα1-hMOG-35-55 and 0.089 µM for DRhQ. In a competitive experiment, DRhQ showed higher activity against rhMIF to bind CD74 compared to the DRα1-hMOG-35-55 (FIG. 6B).

FIGS. 7A and 7B are graphs showing effect of constructs in EAE mice. C57BL/6 WT male mice between 8 and 12 weeks of age were immunized as described in Material and Methods. DRhQ or DRα1-hMOG-35-55 protein (FIG. 7A) or DRα1-nMOG-35-55 or DRmQ (FIG. 7B) (100 µg in 0.1 ml) was injected s.c. daily for 5 days beginning at an EAE score of ≥2.0 and the mice were scored for clinical signs of EAE (top panels). Mean EAE scores and SDs for mouse groups were calculated for each day from day 8 through day 27 post-immunization and summed for each mouse by numerically integrating the EAE score curve over the entire experiment (CDI, represents total disease load; bottom panels).

Figure 8:
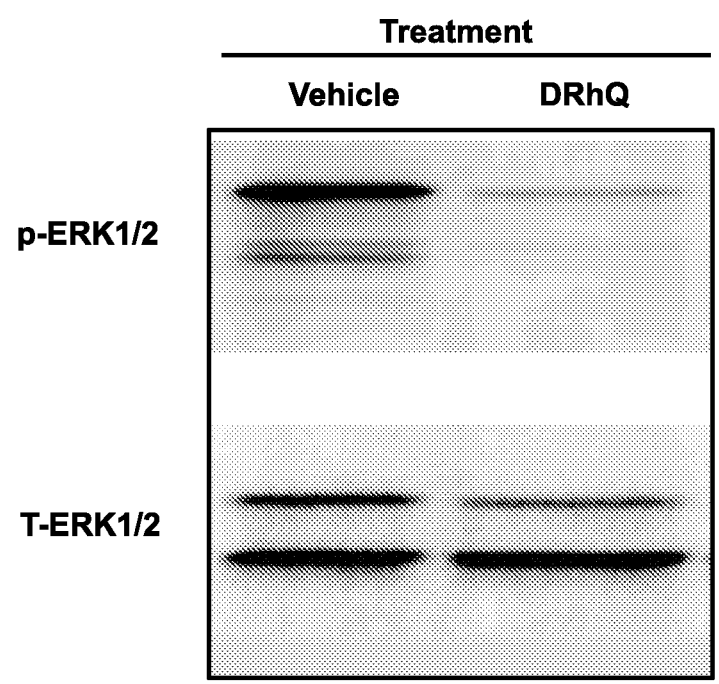

FIG. 8 is a panel showing ERK1/2 phosphorylation assay. Two million splenocyte cells from EAE mice were treated with vehicle, DRhQ or DRα1-hMOG-35-55 for 30 minutes and then cells were lysed in the presence of protease and phosphatase inhibitor. Supernatants were analyzed by electrophoresis and Western blot to evaluate P-ERK1/2 and total ERK1/2 (T-ERK1/2). DRα1-hMOG (not shown) and DRhQ were able to downregulate ERK1/2 phosphorylation in vitro.

Figure 9A:
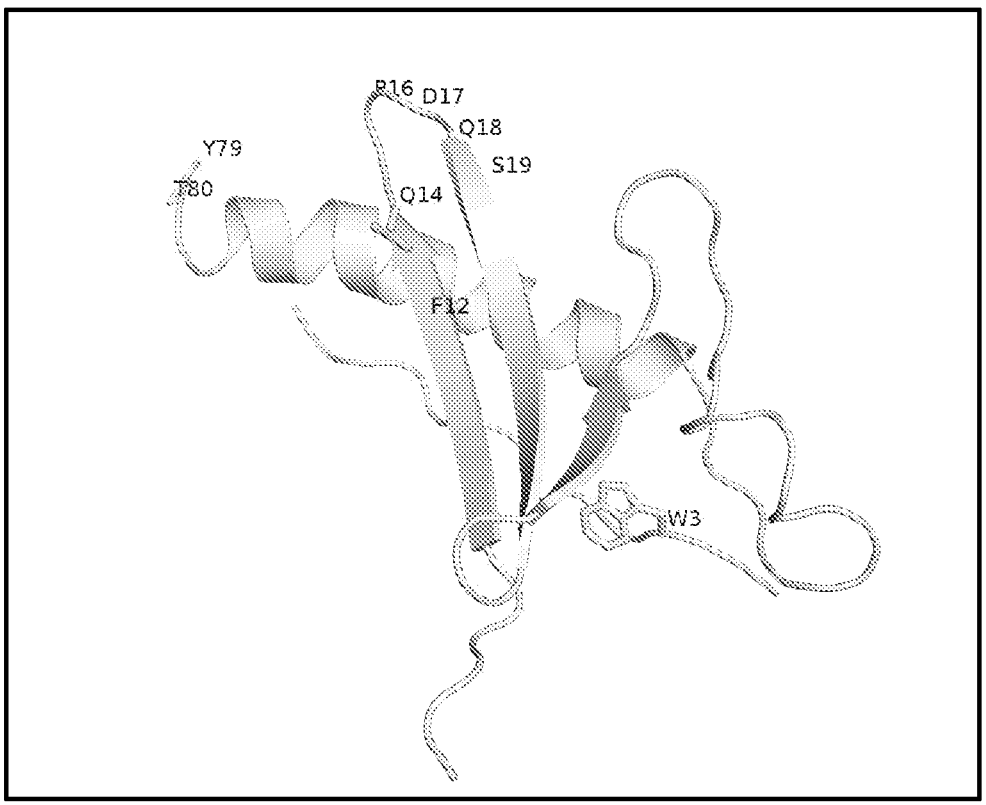
Figure 9B:
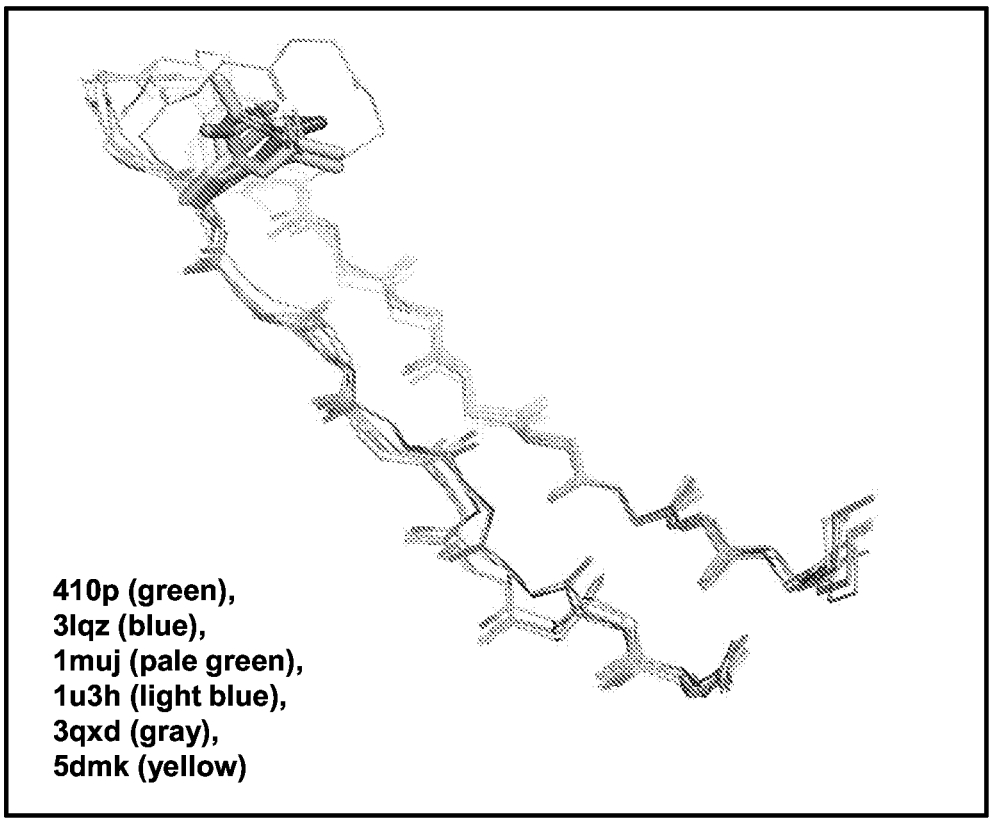

FIG. 9A is a cartoon-rendered structure model of DRhQ that shows the position of relevant amino acid residues in the DRα1-hMOG-35-55 construct and that were shown by the docking model to contact CD74. The Q residue side chain is highlighted at position 14. The antigenic MOG peptide is shown in light gray and the side chain for W3 in the MOG peptide is displayed. FIG. 9B shows several α1 domains from molecules described in FIG. 1 (from the Protein Data Bank) and their β1-strand-loop-β-strand region were aligned using PyMOL (Schrodinger, Portland OR). Position 14 has been highlighted as sticks. Note that the amino acid residues numbering in FIG. 1 differs from the numbering in the crystal structures: Q18 in FIG. 1 corresponds to amino acid residue 14 in most of the crystal structures and is located at the end of the β-strand 1 of the domain.

SEQUENCE LISTING

Any nucleic acid and amino acid sequences listed herein or in the accompanying sequence listing are shown using standard single letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Corrected_Sequence_Listing.txt, which was created on May 12, 2021, and is 28,237 bytes, which is incorporated by reference herein.

SEQ ID NO: 1 is the amino acid sequence of an exemplary human DRα1
polypeptide with L14Q substitution (underlined):
IKEEHVIIQAEFYQNPDQSGEFMFDFDGDEIFHVDMAKKETVWRLEEFGRFASFEAQGAL
ANIAVDKANLEIMTKRSNYTPITN SEQ ID NO: 2 is the amino acid sequence of an exemplary DRhQ
polypeptide. DRhQ includes the antigenic peptide human MOG-35-55
(underlined), spacers (bold), a thrombin cleavage site (capitalized
italics) between the two spacers and the modified DRα1 domain (black
capitalized text). The L14Q (L50Q) mutation in the DRα1 portion is
underlined:
MEVGWYRPPFSRVVHLYRNGKGGGGS_LVPR_GSGGGGIKEEHVIIQAEFYQNPDQSGEF
MFDFDGDEIFHVDMAKKETVWRLEEFGRFASFEAQGALANIAVDKANLEIMTKRSNYT
PITN SEQ ID NO: 3 is the amino acid sequence of an exemplary DRmQ
polypeptide. DRmQ includes the antigenic peptide mouse MOG-35-55
(underlined), spacers (bold), a thrombin cleavage site (capitalized -continued
italics) between the two spacers and the modified DRα1 domain (black capitalized text). The L14Q (L50Q) mutation in the DRα1 portion is underlined:
MEVGWYRSPFSRVVHLYRNGKGGGGS_LVPR_GSGGGGIKEEHVIIQAEFYQNPDQSGEF
MFDFDGDEIFHVDMAKKETVWRLEEFGRFASFEAQGALANIAVDKANLEIMTKRSNYT
PITN SEQ ID NO: 4 is an exemplary nucleic acid encoding human L14Q DRα1. The codon encoding the mutation is underlined:
ATCAAAGAAGAACATGTGATCATCCAGGCCGAGTTCTATCAGAATCCTGACCAATCA

GGCGAGTTTATGTTTGACTTTGATGGTGATGAGATTTTCCATGTGGATATGGCAAAG

AAGGAGACGGTCTGGCGGCTTGAAGAATTTGGACGATTTGCCAGCTTTGAGGCTCAA

GGTGCATTGGCCAACATAGCTGTGGACAAAGCCAACTTGGAAATCATGACAAAGCG

CTCCAACTATACTCC

SEQ ID NO: 5 is an exemplary nucleic acid encoding DRhQ. The codon encoding the L14Q (L50Q) mutation in the DRa1 portion is underlined:

ATGGAAGTTGGTTGGTACCGTCCGCCGTTCTCCCGTGTTGTTCACCTGTACCGTAACG

GTAAAGGAGGTGGAGGCTCACTAGTGCCCCGAGGCTCTGGAGGTGGAGGCATCAAA

GAAGAACATGTGATCATCCAGGCCGAGTTCTATCAGAATCCTGACCAATCAGGCGA

GTTTATGTTTGACTTTGATGGTGATGAGATTTTCCATGTGGATATGGCAAAGAAGGA

GACGGTCTGGCGGCTTGAAGAATTTGGACGATTTGCCAGCTTTGAGGCTCAAGGTGC

ATTGGCCAACATAGCTGTGGACAAAGCCAACTTGGAAATCATGACAAAGCGCTCCA

ACTATACTCCGATCACCAATTAA

SEQ ID NO: 6 is an exemplary nucleic acid encoding DRmQ. The codon encoding the L14Q (L50Q) mutation in the DRa1 portion is underlined:

ATGGAAGTTGGTTGGTACCGTTCCCCGTTCTCCCGTGTTGTTCACCTGTACCGTAACG

GTAAAGGAGGTGGAGGCTCACTAGTGCCCCGAGGCTCTGGAGGTGGAGGCATCAAA

GAAGAACATGTGATCATCCAGGCCGAGTTCTATCAAAATCCTGACCAATCAGGCGA

GTTTATGTTTGACTTTGATGGTGATGAGATTTTCCATGTGGATATGGCAAAGAAGGA

GACGGTCTGGCGGCTTGAAGAATTTGGACGATTTGCCAGCTTTGAGGCTCAAGGTGC

ATTGGCCAACATAGCTGTGGACAAAGCCAACTTGGAAATCATGACAAAGCGCTCCA

ACTATACTCCGATCACCAATTAA

SEQ ID NOs: 7-19 are human and mouse Class II α1 domains.

SEQ ID NOs: 20-23 are human and mouse DRα1-MOG-35-55 constructs.

SEQ ID NOs: 24-31 are full length and P1-P7 peptides of DRα1.

SEQ ID NOs: 32-64 are exemplary antigenic peptides.

DETAILED DESCRIPTION

In both the animal model of MS, experimental autoimmune encephalomyelitis (EAE), and in MS subjects, multiple lines of evidence support the role of autoreactive, myelin-specific, $CD4^+$ T cells in the autoimmune disease process (Steinman, *Cell* 85:299-302, 1996; Zamvil et al., *Annu. Rev. Immunol.* 8:579-621, 1990; Chitnis, *Int. Rev. Neurobiol.* 79:43-72, 2007). Key cytokines thought to drive the early inflammatory stage of MS to a chronic progressive phase are macrophage migration inhibitory factor (MIF), the first described cytokine, and its ancestral functional homolog, D-dopachrome tautomerase (D-DT) (Chitnis, *Int. Rev. Neurobiol.* 79:43-72, 2007). MIF and D-DT levels are increased and have been implicated as markers of clinical worsening in MS and as a requirement for disease progression in EAE (Benedek et al., *Proc. Natl. Acad. Sci. USA* 114:E8421-E8429, 2017; Niino et al., *J. Neurol. Sci.* 179 (S1-2):127-131, 2000; Powell et al., *J. Immunol.* 175:5611-5614, 2005; Meza-Romero et al., *J. Immunol.* 192:4164-4173, 2014).

A potent biological therapy called RTL1000 and a second-generation derivative, DRα1-human(h)MOG-35-55, that bind tightly to the MIF/D-DT receptor, CD74, and competitively inhibit MIF/D-DT binding and downstream signaling through phosphorylated extracellular signal-related kinases (p)ERK1/2 has previously been developed (Vandenbark et al., *J. Immunol.* 171:127-133, 2003; Benedek et al., *J. Neuroinflammation* 12:123, 2015). RTL1000 and DRα1-hMOG-3-55 can treat mice with EAE after onset of clinical signs, resulting in the inhibition of T cell and macrophage activation and migration into the central nervous system and reduced disease severity (Vandenbark et al., *J. Immunol.* 171:127-133, 2003; Benedek et al., *Eur. J. Immunol.* 43:1309-1321, 2013; Meza-Romero et al., *J. Immunol.* 192: 4164-4173, 2014). RTL treatment was also found to enhance anti-inflammatory macrophage/microglia cell numbers, promote re-myelination, and reduce the severity of acute and chronic EAE (Meza-Romero et al., *J. Immunol.* 192:4164-4173, 2014).

In the present disclosure, the inventors have identified an amino acid substitution of glutamine for leucine at position 50 (L50Q) of the DRα1-hMOG-35-55 construct (termed DRhQ) that alters the affinity of the construct for CD74, with a 8-10-fold increase in binding capacity. This substitution did not affect the structure of the molecule as evaluated by circular dichroism and antibody probing and the increased binding affinity translated into a commensurate ability of DRhQ to competitively inhibit MIF binding to its cognate CD74 receptor. Treatment of WT C57BL/6 mice with DRhQ reduced pERK1/2 phosphorylation in vitro in splenocytes to a background level. Finally, the L50Q substitution significantly enhanced the ability of the construct to treat ongoing clinical signs of severe EAE.

I. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. All GenBank Accession numbers mentioned herein are incorporated by reference in their entirety as present in GenBank on Oct. 5, 2018. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" or "antigenic peptide" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 8 amino acids (such as about 8-50 or 8-23 amino acids) in a unique spatial conformation. Methods of determining spatial conformation of epitopes include, for example, x-ray crystallography and two-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. A tissue-specific antigen may be expressed by more than one tissue, such as, but not limited to, an antigen that is expressed in the central or peripheral nervous system.

CD74: Also known as CD74 molecule, major histocompatibility complex, class II invariant chain or Ii. CD74 is a chaperone regulating antigen presentation. It is also a cell surface receptor for macrophage migration inhibitory factor (MIF). Nucleic acid and protein sequences for CD74 are publicly available. For example, GenBank Accession Nos. NM_001025158, NM_004355, and NM_001025159 disclose exemplary human CD74 nucleic acid sequences, and GenBank Accession Nos. NP_001020329, NP_004346, and NP_001020330 disclose exemplary human CD74 amino acid sequences. Similarly, GenBank Accession Nos. NM_001042605 and NM_010545 disclose exemplary mouse CD74 nucleic acid sequences, and GenBank Accession Nos. NP_001036070 and NP_034675 disclose exemplary mouse CD74 amino acid sequences. Each of these sequences is incorporated herein by reference as present in GenBank on Oct. 5, 2018.

Control: A "control" refers to a sample or standard used for comparison with an experimental sample. In some embodiments, the control is a sample obtained from a healthy subject or population of healthy subjects. In other embodiments, the control is a historical control or standard reference value or range of values (such as a previously tested control sample, such as a group of samples that represent baseline or normal values, such as the level of CD74 expression or activity in healthy subjects). In further examples, the control is from a subject prior to treatment (such as CD74 expression or activity level prior to treatment with an MHC class II β1α1 polypeptide or an MHC class II α1 domain polypeptide).

Domain: A discrete part of an amino acid sequence of a polypeptide or protein that can be equated with a particular function. For example, the α and β polypeptides that constitute a MHC class II molecule are each recognized as having two domains, α1, α2 and β1, β2, respectively. The various domains are typically joined by linking amino acid sequences. In one embodiment, the entire domain sequence is included in a recombinant molecule by extending the sequence to include all or part of the linker or the adjacent domain. For example, when selecting the α1 domain of an MHC class II molecule, the selected sequence may extend from amino acid residue number 1 of the α chain, through the entire α1 domain to amino acid 84 at the carboxy terminus of the α1 domain. The precise number of amino acids in the various MHC molecule domains varies depending on the species of mammal, as well as between classes of genes within a species. The selection of a sequence for use in a recombinant molecule requires maintenance of the domain function rather than a precise structural definition based on the number of amino acids. One of ordinary skill in the art will appreciate that domain function may be maintained even if somewhat less than the entire amino acid sequence of the selected domain is utilized. For example, a number of amino acids at either the amino or carboxy termini of the α1 domain may be omitted without affecting domain function. The functional activity of a particular selected domain may be assessed in the context of the MHC class II polypeptides provided by this disclosure (e.g., the α1 polypeptides), for example, T cell proliferation and/or CD74 binding assays.

Effective amount: A dose or quantity of a specified compound sufficient to inhibit advancement, or to cause regression of a disease or condition, or which is capable of relieving symptoms caused by the disease or condition. For instance, this can be the amount or dose of a disclosed MHC molecule required to treat or inhibit a disorder, such as an inflammatory and/or autoimmune disorder. In one embodiment, an effective amount is the amount that alone, or together with one or more additional therapeutic agents, induces the desired response in a subject, such as treating or inhibiting an inflammatory or autoimmune disorder or other disease or disorder.

Inflammation: A localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods, such as the number of white blood cells, the number of polymorphonuclear neutrophils (PMN), a measure of the degree of PMN activation, such as luminal enhanced chemiluminescence, or a measure of the amount of cytokines present.

A primary inflammation disorder is a disorder that is caused by the inflammation itself. A secondary inflammation disorder is inflammation that is the result of another disorder. Inflammation can lead to a host of inflammatory diseases, including, but not limited to rheumatoid arthritis, osteoarthritis, inflammatory lung disease (including chronic obstructive pulmonary lung disease), inflammatory bowel disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis) and the like. Auto-immune disorders which include an inflammatory component (including, but not limited to multiple sclerosis) are also considered to be inflammatory disorders.

Inhibiting or treating a disease: "Inhibiting" a disease refers to inhibiting the full development of a disease, for example in a person who is known to have a predisposition to a disease such as an inflammatory or autoimmune disorder. Inhibition of a disease can span the spectrum from partial inhibition to substantially complete inhibition of the disease, for example in a subject who has a disease or disorder or is at risk of developing a disease or disorder. In some examples, the term "inhibiting" refers to reducing or delaying the onset or progression of a disease. "Treating" a disease refers to a therapeutic intervention that ameliorates a sign or symptom of a disease or pathological condition, such as a sign or symptom of an inflammatory or autoimmune disorder. A subject to be administered an effective amount of the pharmaceutical compound to inhibit or treat the disease or disorder can be identified by standard diagnosing techniques for such a disorder, for example, symptoms, basis of family history, or risk factor to develop the disease or disorder.

Linker: A molecule that covalently links two molecules (such as two polypeptides). Linkers (such as a peptide linker or a chemical linker) may be included in the recombinant MHC polypeptides of the present disclosure for example between an α1 domain and an antigenic peptide. Peptide linker sequences, which are generally between 2 and 25 amino acids in length (such as 5-10, 10-15, 15-20, or 20-25 amino acids), include, but are not limited to, the glycine(4)-serine spacer described by Chaudhary et al. (Nature 339: 394-397, 1989). Similarly, chemical linkers (such as thiol bonds or crosslinking agents) can also be used.

MHC Class II: MHC Class II molecules are formed from two noncovalently associated proteins, the α chain and the β chain. The α chain comprises α1 and α2 domains, and the β chain comprises β1 and β2 domains. The cleft into which the antigen fits is formed by the interaction of the α1 and β1 domains. The α2 and β2 domains are transmembrane Ig-fold like domains that anchor the α and β chains into the cell membrane of the APC. MHC Class II complexes, when associated with antigen (and in the presence of appropriate co-stimulatory signals) stimulate CD4 T-cells. The primary functions of CD4 T-cells are to initiate the inflammatory response, to regulate other cells in the immune system, and to provide help to B cells for antibody synthesis.

Pharmaceutically acceptable carriers: *Remington: The Science and Practice of Pharmacy*, The University of the Sciences in Philadelphia, Editor, Lippincott, Williams, & Wilkins, Philadelphia, PA, 21st 30 Edition (2005), describes compositions and formulations suitable for pharmaceutical delivery of the proteins herein disclosed.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Polypeptides or domains thereof that have a significant amount of sequence identity and function the same or similarly to one another—for example, the same protein in different species—can be called 'homologs.' Methods of alignment of sequences for comparison are well known in the art. Various programs and alignment algorithms are described in: Smith & Waterman, *Adv. Appl. Math.* 2: 482, 1981; Needleman & Wunsch, *J. Mol. Biol.* 48: 443, 1970; Pearson & Lipman, *Proc. Natl. Acad. Sci. USA* 85: 2444, 1988; Higgins & Sharp, *Gene,* 73: 237-244, 1988; Higgins & Sharp, *Comput. Appl. Biosci.* 5: 151-153, 1989; Corpet et al., *Nucl. Acids Res.* 16, 10881-90, 1988; Huang et al., *Comput. Appl. Biosci.* 8, 155-65, 1992; and Pearson, *Methods Mol. Biol.* 24:307-331, 1994. Altschul et al. (*J. Mol. Biol.* 215:403-410, 1990) presents a detailed consideration of sequence alignment methods and homology calculations. The NCBI Basic Local Alignment Search Tool (BLAST) is available from several sources, including the National Center for Biotechnology Information (NCBI, Bethesda, MD) and on the Internet, for use in connection with the sequence analysis programs blastp, blastn, blastx, tblastn and tblastx.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Subject: Living multi-cellular vertebrate organisms, a category that includes both human and non-human mammals.

II. DRα Domains

Disclosed herein are isolated recombinant polypeptides which include an MHC class II DRα1 domain or fragment thereof and do not include MHC class II α2, β1, or β2 domains, and include a substitution of glutamine (Q) for the leucine (L) present at the amino acid position corresponding to amino acid 14 of SEQ ID NO: 1. The amino acid sequences of mammalian MHC class II DRα chain proteins, as well as nucleic acids encoding these proteins, are well known in the art and available from numerous sources including GenBank. Exemplary sequences are provided in Das et al. (*Proc. Natl. Acad. Sci. USA* 80:3543-3547, 1983) (human HLA DRα) which is incorporated by reference herein. An exemplary human DRα polypeptide is GenBank Accession No. NP_061984 (incorporated herein by reference as present in GenBank on Oct. 5, 2018). Additional MHC class II DRα polypeptides can be identified by one of ordinary skill in the art, for example, from public databases, such as the IMGT/HLA database (available on the world wide web at ebi.ac.uk/imgt/hla/).

In a particular embodiment, the MHC class II α1 domain is a human HLA-DRA polypeptide. The α1 domain is well defined in mammalian MHC class II α chain proteins. In some examples, MHC class II α chains include a leader sequence involved in trafficking the polypeptide that is proteolytically removed to produce the mature α polypeptide.

An α1 domain may include about amino acid residues 1-90 of the mature α chain, but one of ordinary skill in the art will recognize that the C-terminal cut-off of this domain is not necessarily precisely defined, and, for example, might occur at any point between amino acid residues 70-100 of the mature α chain. In some examples, the α1 domain includes amino acids 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, or 1-100 of a mature MHC class II DRα domain. In other examples, an α1 domain includes about residues 20-120 (such as about residues 20-110, 24-110, 24-109, 25-100, 25-109, 26-110, 26-109, 30-120, 32-120, 32-115, 26-90, 26-85, 26-84, or other overlapping regions) of a full length DR α1 polypeptide. In some examples, the DRα1 domain does not include an N-terminal methionine; however, an N-terminal methionine can be present, for example as a result of expression in a bacterial, yeast, or mammalian system.

In further examples, the DRα1 domain can include deletion or addition of a few amino acids at the 5'- and/or 3'-end, such as addition or deletion of about 1-25 amino acids, such as addition or deletion of 1, 2, 3, 4, 5, 6, 7, 8, 9, 10, 11, 12, 13, 14, 15, 16, 17, 18, 19, 20, 21, 22, 23, 24, or 25 amino acids from the 5'- or 3'-end, or combinations thereof (such as a deletion from one end and an addition to the other end). The composition of the α1 domain may also vary outside of these parameters depending on the mammalian species and the particular α chain in question. One of ordinary skill in the art will appreciate that the precise numerical parameters of the amino acid sequence are less important than the maintenance of domain function (for example, CD74 binding or down-regulation).

In some embodiments, disclosed are recombinant polypeptides that include a DRα1 domain including a glutamine residue at a position corresponding to amino acid position 14 of SEQ ID NO: 1. The recombinant polypeptides do not include MHC class II α2, β1, or β2 domains. In some examples, the recombinant DRα1 polypeptide includes, consists essentially of, or consists of the amino acid sequence of SEQ ID NO: 1. In additional embodiments, the recombinant polypeptide has a sequence at least 75%, 85%, 90%, 95%, 96%, 97%, 98% or 99% identical to SEQ ID NO: 1 or a fragment thereof. For example, the DRα1 polypeptide can be a homolog or ortholog of SEQ ID NO: 1 with an amino acid sequence at least 85%, 90%, 95%, 96%, 97%, 98% or 99% identical to SEQ ID NO: 1 or a fragment thereof. Exemplary sequences can be obtained using computer programs that are readily available on the world wide web and the amino acid sequences set forth herein. In some examples, the homolog retains a function of the polypeptide of SEQ ID NO: 1 such as an altered secondary structure, binding to CD74, and/or inhibiting EAE in mice.

In other embodiments, disclosed are recombinant polypeptides that include a DRα1 domain or a fragment thereof including a glutamine residue at a position corresponding to amino acid position 14 of SEQ ID NO: 1 and an antigenic peptide. The recombinant polypeptides do not include MHC class II α2, β1, or β2 domains. In some examples, the recombinant polypeptide further includes a linker (for example, a linker between the DRα1 polypeptide and the antigenic peptide). The linker may be a peptide linker or a chemical linker (such as a chemical cross-linker).

In some embodiments, the antigenic peptide is human or mouse myelin oligodendrocyte glycoprotein (MOG) 35-55. Thus, in some embodiments, the recombinant polypeptide includes, consists essentially of, or consists of the amino acid sequence of SEQ ID NO: 2 or SEQ ID NO: 3. In additional embodiments, the recombinant polypeptide has a sequence at least 75%, 85%, 90%, 95%, 96%, 97%, 98% or 99% identical to SEQ ID NO: 2 or SEQ ID NO: 3 or a fragment thereof. For example, the DRα1 portion of the polypeptide can be a homolog or ortholog of SEQ ID NO: 1 with an amino acid sequence at least 85%, 90%, 95%, 96%, 97%, 98% or 99% identical to SEQ ID NO: 1 or a fragment thereof. Exemplary sequences can be obtained using computer programs that are readily available on the world wide web and the amino acid sequences set forth herein. In some examples, the polypeptide retains a function of the polypeptide of SEQ ID NO: 2 or SEQ ID NO: 3 such as an altered secondary structure, binding to CD74, and/or inhibiting EAE in mice. Additional antigenic peptides that can be included in the polypeptide are discussed below.

Minor modifications of the recombinant polypeptides (e.g., SEQ ID NOs: 1-3) may result in polypeptides which have substantially equivalent activity (for example, as compared to SEQ ID NOs: 1-3). Such modifications may be deliberate, as by site-directed mutagenesis, or may be spontaneous. All of the polypeptides produced by these modifications are included herein. Thus, a specific, non-limiting example of an MHC class II DRα1 polypeptide is a conservative variant of any one of SEQ ID NOs: 1-3 (such as a conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions).

Nucleic acid molecules encoding the disclosed recombinant DRα1 polypeptides (e.g., encoding any one of SEQ ID NOs: 1-3) and/or any homologs or variants thereof can be produced by standard approaches, such as amplification by the polymerase chain reaction (PCR). In some examples, the recombinant polypeptide is encoded by a nucleic acid including or consisting of the nucleic acid sequence of any one of SEQ ID NOs: 4-6. In additional embodiments, the nucleic acid has a sequence at least 75%, 85%, 90%, 95%, 96%, 97%, 98% or 99% identical to any one of SEQ ID NOs: 4-6 or a fragment thereof.

In some embodiments, the recombinant polypeptide (e.g., SEQ ID NOs: 1-3) can be expressed in prokaryotic or eukaryotic cells from a nucleic acid construct encoding the recombinant polypeptide (such as a nucleic acid construct including any one of SEQ ID NOs: 4-6). Nucleic acid constructs (such as expression constructs) encoding the recombinant polypeptides may also include regulatory elements such as promoters, enhancers, and/or 3' regulatory regions, the selection of which will be determined based upon the type of cell in which the protein is to be expressed. The constructs are introduced into a vector suitable for expressing the recombinant polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), phage T7, and lambda P$_L$ promoters. Methods and plasmid vectors for producing heterologous proteins in bacteria or mammalian cells are described in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); and Ausubel et al., *Short Protocols in Molecular Biology: A Compendium of Methods from Current Protocols in Molecular Biology*, 4th ed., Wiley & Sons, 1999.

Suitable prokaryotic cells for expression of large amounts of proteins include *Escherichia coli* and *Bacillus subtilis*. Often, proteins expressed at high levels are found in insoluble inclusion bodies; methods for extracting proteins from these aggregates are described for example, by Sambrook et al. (2001, see chapter 15). Recombinant expression of recombinant polypeptides in prokaryotic cells may alternatively be conveniently obtained using commercial systems designed for optimal expression and purification of fusion proteins. Such fusion proteins typically include a tag that facilitates purification. Examples of such systems include: the pMAL protein fusion and purification system (New England Biolabs, Inc., Beverly, MA); the GST gene fusion system (Amersham Pharmacia Biotech, Inc., Piscataway, NJ); and the pTrcHis expression vector system (Invitrogen, Carlsbad, CA). Additional systems include the His6-tag (e.g., Roche Applied Science, Mannheim, Germany) or streptavidin binding peptide (e.g., Sigma-Aldrich, St. Louis, MO). For example, the pMAL expression system utilizes a vector that adds a maltose binding protein to the expressed protein. The fusion protein is expressed in *E. coli*. and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The recombinant polypeptides can also be expressed in eukaryotic expression systems, including *Pichia pastoris*, *Drosophila*, Baculovirus and/or Sindbis expression systems produced by Invitrogen (Carlsbad, CA). Eukaryotic cells such as Chinese Hamster ovary (CHO), monkey kidney (COS), HeLa, *Spodoptera frugiperda*, and *Saccharomyces cerevisiae* may also be used to express recombinant polypeptides. Regulatory regions suitable for use in these cells include, for mammalian cells, viral promoters such as those from CMV, adenovirus or SV40, and for yeast cells, the promoter for 3-phosphoglycerate kinase or alcohol dehydrogenase.

The vectors can be introduced into recipient cells (such as eukaryotic cells) as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

A DRα1 polypeptide (such as those described herein) produced in mammalian cells may be extracted following release of the protein into the supernatant and may be purified using an immunoaffinity column prepared using anti-MHC or other antibodies. Alternatively, the polypeptide may be expressed as a chimeric protein with, for example, β-globin. Antibody to β-globin is thereafter used to purify the chimeric protein. Corresponding protease cleavage sites engineered between the β-globin gene and the nucleic acid sequence encoding the recombinant polypeptide are then used to separate the two polypeptide fragments from one another after translation. One useful expression vector for generating β-globin chimeric proteins is pSG5 (Stratagene, La Jolla, CA).

Expression of the recombinant polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells. In other examples, the recombinant polypeptide can be modified (for example, by site-directed mutagenesis) to include desired post-translational modification sites such as one or more sites for N-linked glycosylation, phosphorylation, or other modifications.

Purification of the expressed protein is generally performed in a basic solution (typically around pH 10) containing 6M urea. Folding of the purified protein is then achieved by dialysis against a buffered solution at neutral pH (typically phosphate buffered saline at around pH 7.4). Other methods of protein purification are also known and can be used with the recombinant polypeptides disclosed herein.

III. Antigenic Peptides

In some embodiments, the recombinant polypeptides disclosed herein comprise antigenic peptides covalently linked to the DRα1 domain—either directly or via a peptide or chemical linker. The presentation of antigen in MHC complexes on the surface of APCs generally does not involve a whole antigenic peptide (see for example U.S. Pat. No. 5,468,481). Rather, a peptide located in the groove between the β1 and α1 domains in the case of MHC II or the α1 and α2 domains in the case of MHC1 is typically a small linear fragment of a whole polypeptide antigen. As discussed in Janeway & Travers (*Immunobiology: The Immune System in Health and Disease,* 1997), peptides located in the peptide groove of MHC class I molecules are constrained by the size of the binding pocket and are typically 8-15 amino acids long (such as 8, 9, 10, 11, 12, 13, 14, or 15 amino acids), more typically 8-10 amino acids in length (but see Collins et al., *Nature* 371:626-629, 1994 for possible exceptions). In contrast, peptides located in the peptide groove of MHC class II molecules are not constrained in this way and are often larger, typically at least 3-50 amino acids in length (such as 8-30, 10-25, or 15-23 amino acids in length). In some examples, the peptide located in the peptide groove of an MHC class II molecule is about 15-23 amino acids in length. Peptide fragments can be prepared by standard approaches, such as use of synthetic peptide synthesis machines or they can be expressed as part of a recombinant polypeptide.

In some examples, an antigenic peptide includes a peptide from a neuronal or central nervous system protein, such as a myelin protein (for example, myelin oligodendrocyte glycoprotein (MOG), myelin basic protein (MBP), or proteolipid protein (PLP)). In specific examples the antigenic peptide includes a human or mouse MOG-35-55 peptide, exemplified by amino acids 1-21 of SEQ ID NO: 2 or 1-21 of SEQ ID NO: 3, respectively. In other examples, an antigenic peptide is a peptide from a retinal protein, such as interphotoreceptor retinoid binding protein (IRBP), arrestin, phosducin, or recoverin. Additional antigenic peptides include peptides from type II collagen (collagen II), fibrinogen-α, vimentin, α-enolase, human cartilage glycoprotein-39, a2 gliadin, or insulin. In some examples, an antigenic peptide includes a post-translational modification, such as phosphorylation, glycosylation, or citrullination. Sequences of exemplary antigenic peptides are provided in Table 1 and in International Pat. Publ. No. WO 2012/103365 and U.S. Pat. Publ. No. 2012/0276127, both of which are incorporated herein by reference in their entirety. One of ordinary skill in the art can identify additional antigenic peptides relevant to a particular disease or disorder.

TABLE 1

Exemplary antigenic peptides

| Antigenic Peptide | Sequence | SEQ ID NO: |
|---|---|---|
| Human MOG-35-55 | MEVGWYRPPFSRVVHLYRNGK | 32 |
| Mouse MOG-35-55 | MEVGWYRSPFSRVVHLYRNGK | 33 |
| Interphotoreceptor retinoid-binding protein 1177-1191 | ADGSSWEGVGVVPDV | 34 |
| Arrestin 291-310 | NRERRGIALDGKIKHEDTNL | 35 |
| Phosducin 65-96 | KERMSRKMSIQEYELI HQDKEDEGCLRKYRRQ | 36 |
| Recoverin 48-52 | QFQSI | 37 |
| Recoverin 64-70 | KAYAQHV | 38 |
| Recoverin 62-81 | PKAYAQHVFRSFDANSDGTL | 39 |
| Recoverin 149-162 | EKRAEKIWASFGKK | 40 |
| Collagen II 261-274 | AGFKGEQGPKGEPG | 41 |
| collagen II 259-273 | GIAGFKGEQGPKGEP | 42 |
| collagen II 257-270 | EPGIAGFKGEQGPK | 43 |
| Modified collagen II 257-270 | APGIAGFKAEQAAK | 44 |
| fibrinogen-α 40-59 | VERHQSACKDSDWPFCSDED | 45 |
| fibrinogen-α 616-625 | THSTKRGHAKSRPVRGIHTS | 46 |
| fibrinogen-α 79-91 | QDFTNRINKLKNS | 47 |
| fibrinogen-α 121-140 | NNRDNTYNRVSEDLRSRIEV | 48 |
| vimentin 59-79 | GVYATRSSAVRLRSSVPGVRL | 49 |
| vimentin 26-44 | SSRSYVTTSTRTYSLGSAL | 50 |
| vimentin 256-275 | IDVDVSKPDLTAALRDVRQQ | 51 |
| vimentin 415-433 | LPNFSSLNLRETNLD LPL | 52 |
| α-enolase 5-21 | KIHAREIFDSRGNPTVE | 53 |

TABLE 1-continued

Exemplary antigenic peptides

| Antigenic Peptide | Sequence | SEQ ID NO: |
|---|---|---|
| human cartilage glycoprotein 39 259-271 | PTFGRSFTLASSE | 54 |
| Myelin basic protein 85-99 | ENPVVHFFKNIVTPR | 55 |
| Myelin basic protein 145-164 | VDAQGTLSKIFKLGGRDSRS | 56 |
| Proteolipid protein 139-151 | CHCLGKWLGHPDKFVG | 57 |
| Proteolipid protein 95-116 | GAVRQIFGDYKTTICGKGLSAT | 58 |
| MOG 1-25 | GQFRVIGPRHPIRALVGDEV | 59 |
| MOG 94-116 | GGFTCFFRDHSYQEEAAMELKVE | 60 |
| MOG 145-160 | VFLCLQYRLRGKLRAE | 61 |
| MOG 194-208 | LVALIICYNWLHRRL | 62 |
| α2-gliadin 61-71 | PQPELPYPQP | 63 |
| α2-gliadin 58-77 | LQPFPQPQLPYPQPQLPYPQ | 64 |

In some examples, the antigenic peptide is covalently linked to the MHC class II DRα1 polypeptide by operably linking a nucleic acid sequence encoding the selected antigenic peptide to the 5' end of the construct encoding the DRα1 polypeptide such that, in the expressed peptide, the antigenic peptide is linked to the amino-terminus of the DRα1 domain. In other examples, the antigenic peptide is covalently linked to the DRα1 polypeptide by operably linking a nucleic acid sequence encoding the selected antigen to the 3' end of the construct encoding the DRα1 polypeptide such that, in the expressed peptide, the antigenic peptide is linked to the carboxy-terminus of the DRα1 domain. One convenient way of obtaining this result is to incorporate a sequence encoding the antigenic peptide into the PCR primers used to amplify the DRα1 domain coding region. In some examples, a sequence encoding a linker peptide sequence is included between the antigenic peptide and the DRα1 polypeptide. However, it is not necessary that the antigenic peptide be ligated exactly at the 5' end (or 3' end) of the MHC class II α1 domain coding region. For example, the antigenic peptide coding region may be inserted into the α1 domain within the first few (typically within the first 10) codons of the 5' or 3' end of the DRα1 domain coding sequence.

In some embodiments, a genetic system for linkage of the antigenic peptide to the DRα1 domain is particularly useful where a number of DRα1 domains with differing antigenic peptides are to be produced. The described system permits the construction of an expression vector in which a unique restriction site is included in the DRα1 domain (e.g., at the 5' or 3' end of the α1 domain). In conjunction with such a construct, a library of antigenic peptide encoding sequences is made, with each antigen-coding region flanked by sites for the selected restriction enzyme. The inclusion of a particular antigen into the DRα1 domain is then performed simply by (a) releasing the antigen-coding region with the selected restriction enzyme, (b) cleaving the DRα1 domain construct with the same restriction enzyme, and (c) ligating the antigen coding region into the DRα1 domain construct. In this manner, a large number of DRα1 domain-peptide antigen constructs can be made and expressed in a short period of time.

In some examples, the antigen is covalently linked to the DRα1 domain polypeptide by a peptide linker. In some examples, the linker includes one or more (for example, 1, 2, 3, 4, or more) glycine-serine spacers, for example GGGGS (SEQ ID NO: 52). In some examples, the linker includes two glycine-serine spacers. In a non-limiting example, the recombinant polypeptide may include a first glycine-serine spacer, a thrombin cleavage site, and a second glycine-serine spacer between the antigenic peptide and the DRα1 polypeptide.

In some examples, the antigen is covalently linked to the DRα1 domain polypeptide by a disulfide bond. In some examples, the disulfide linkage is utilizing a naturally occurring cysteine residue in the DRα1 domain polypeptide (such as a cysteine residue in the DRα1 domain). One of ordinary skill in the art can identify a suitable cysteine residue in a DRα1 domain polypeptide. In other examples, the disulfide linkage is formed utilizing a non-naturally occurring cysteine residue in the DRα1 domain polypeptide, such as a cysteine residue introduced in the DRα1 domain polypeptide by mutagenesis. In further examples, the disulfide linkage is formed utilizing a naturally occurring cysteine residue in the peptide antigen. In still further examples, the disulfide linkage is formed utilizing a non-naturally occurring cysteine residue in the peptide antigen, such as a cysteine residue introduced in the peptide antigen by mutagenesis.

IV. Methods of Treating or Inhibiting Disorders

Disclosed herein are methods of treating or inhibiting disorders in a subject, including but not limited to inflammatory and/or autoimmune disorders. The disclosed methods include administering to a subject a recombinant polypeptide comprising an MHC class II DRα1 domain polypeptide with a glutamine residue at a position corresponding to amino acid position 14 of SEQ ID NO: 1 (exemplified by SEQ ID NO: 1) or the recombinant polypeptide comprising MHC class II DRα1 domain polypeptide with a glutamine residue at a position corresponding to amino acid position 14 of SEQ ID NO: 1 covalently linked to an antigenic peptide (exemplified by SEQ ID NOs: 2 and 3) or a nucleic acid encoding the recombinant polypeptide. In one non-limiting example, the subject has multiple sclerosis and is administered an MHC class II DRα1 domain polypeptide with a glutamine residue at a position corresponding to amino acid position 14 of SEQ ID NO: 1 linked to a MOG-35-55 peptide (such as SEQ ID NO: 2 or SEQ ID NO: 3).

In some embodiments, the methods include selecting a subject with a disorder for treatment and administering an effective amount of the recombinant polypeptide described herein, a nucleic acid encoding the recombinant polypeptide described herein, or a pharmaceutical composition including a disclosed recombinant polypeptide or nucleic acid to the subject.

In some embodiments, the subject has an inflammatory and/or autoimmune disease or disorder, including but not limited to, systemic lupus erythematosus, Sjogren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, celiac disease, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, and Evan's syndrome.

Additional inflammatory diseases include osteoarthritis, inflammatory lung disease (including chronic obstructive pulmonary lung disease), periodontal disease, polymyalgia rheumatica, atherosclerosis, systemic sclerosis, allergic rhinitis, and skin disorders (including dermatomyositis and psoriasis) and the like.

In other embodiments, the subject has a retinal disorder, such as a retinal degeneration, such as retinitis pigmentosa, cone-rod dystrophy, Leber congenital amaurosis, or a maculopathy (for example, age-related macular degeneration, Stargardt-like macular degeneration, vitelliform macular dystrophy (Best disease), Malattia Leventinese (Doyne's honeycomb retinal dystrophy), diabetic maculopathy, occult macular dystrophy, and cellophane maculopathy). In other examples, a retinal disorder includes a retinopathy, such as autoimmune retinopathy, diabetic retinopathy, or vascular retinopathy. In still further examples, a retinal disorder includes retinal detachment or glaucoma. Retinal disorders may be progressive (for example, retinal degeneration or glaucoma) or acute (for example, retinal detachment). In additional examples, the subject is a subject with uveitis or optic neuritis. In other embodiments, the subject has had a stroke (such as ischemic stroke or hemorrhagic stroke). In still further examples, the subject is a subject with substance addiction, for example, a subject with cognitive or neuropsychiatric impairment induced by substance addiction including methamphetamine and alcohol abuse.

In some embodiments, a subject is administered an effective amount of a composition including an DRα1 domain or a portion thereof (such as a portion of an α1 domain which is capable of binding CD74 or decreasing expression and/or activity of CD74) that includes a substitution of glutamine for leucine at a position corresponding to amino acid position 14 of SEQ ID NO: 1. In one example, the composition includes modified DRα1-MOG-35-55 (for example, SEQ ID NO: 2 or SEQ ID NO: 3).

Pharmaceutical compositions that include a recombinant polypeptide or nucleic acid disclosed herein (such as an effective amount of a disclosed recombinant polypeptide or nucleic acid) can be formulated with an appropriate solid or liquid carrier, depending upon the particular mode of administration chosen. The pharmaceutically acceptable carriers and excipients useful in this disclosure include those known to one of ordinary skill in the art. See, e.g., *Remington: The Science and Practice of Pharmacy*, The University of the Sciences in Philadelphia, Editor, Lippincott, Williams, & Wilkins, Philadelphia, PA, 21st Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate.

In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations. The dosage form of the pharmaceutical composition will be determined by the mode of administration chosen.

For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition may be administered by any mode that achieves its intended purpose. Amounts and regimens for the administration of the recombinant polypeptides or portion thereof (or a nucleic acid encoding such polypeptides) can be determined by the attending clinician. Effective doses for therapeutic application will vary depending on the nature and severity of the condition to be treated, the particular DRα1 domain or portion thereof and/or antigenic peptide selected, the age and condition of the patient, and other clinical factors. Typically, the dose range will be from about 0.1 μg/kg body weight to about 100 mg/kg body weight. Other suitable ranges include doses of from about 100 μg/kg to about 50 mg/kg body weight, about 500 μg/kg to about 10 mg/kg body weight, or about 1 mg/kg to about 5 mg/kg body weight, for example, about 1 mg/kg, about 2 mg/kg, about 3 mg/kg, about 4 mg/kg, or about 5 mg/kg. The dosing schedule may vary from once a month to daily depending on a number of clinical factors, such as the subject's sensitivity to the protein. Examples of dosing schedules are about 1 mg/kg administered once a month, bi-weekly, once a week, twice a week, three times a week or daily; a dose of about 2.5 mg/kg once a week, twice a week, three times a week or daily; a dose of about 5 mg/kg once a week, twice a week, three times a week or daily; a dose of about 10 mg/kg once a week, twice a week, three times a week or daily; or a dose of about 30 mg/kg once a week, twice a week, three times a week or daily.

The pharmaceutical compositions that include one or more of the disclosed recombinant polypeptides can be formulated in unit dosage form, suitable for individual administration of precise dosages. In one specific, non-limiting example, a unit dosage can contain from about 1 ng to about 5 g of the recombinant polypeptide (such as about 10 μg to 1 g, about 100 mg to 500 mg, or about 10 mg to 100 mg). The amount of active compound(s) administered will be dependent on the subject being treated, the severity of the affliction, and the manner of administration. Within these bounds, the formulation to be administered will contain a quantity of the active component(s) in amounts effective to achieve the desired effect in the subject being treated.

The recombinant polypeptides can be administered to humans or other animals on whose tissues they are effective in various manners such as topically, orally, intravenously, intramuscularly, intraperitoneally, intranasally, intradermally, intrathecally, subcutaneously, intraocularly, via inhalation, or via suppository. In one example, the compounds are administered to the subject subcutaneously. In another example, the compounds are administered to the subject intravenously.

In some embodiments, the recombinant polypeptides can be included in an inert matrix for topical or local application. In some examples, the formulation can be injected into the eye, for example for intravitreal injection. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including one or more recombinant polypeptides can be applied topically, either in the form of drops or as an aqueous based cream, or can be injected intraocularly. In a formulation for topical application, the recombinant polypeptide is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the recombinant polypeptide over time. In one example, the DRα1 polypeptide can be dissolved in an organic solvent such as DMSO or alcohol and contain a polyanhydride, poly(glycolic) acid, poly(lactic) acid, or polycaprolactone polymer. The recombinant polypeptide can be included in a delivery system that can be implanted at various sites in the eye, depending on the size, shape and formulation of the implant, and the type of transplant procedure. Suitable sites include but are not limited to the anterior chamber, anterior segment, posterior chamber, posterior segment, vitreous cavity, suprachoroidal space, subconjunctiva, episcleral, intracorneal, epicorneal and sclera.

In some examples, an effective amount (for example, a therapeutically effective amount) of a disclosed recombinant polypeptide can be the amount of recombinant polypeptide necessary to treat or inhibit a disorder (such as an inflammatory and/or autoimmune disorder) in a subject. In other examples, a therapeutically effective amount of a disclosed recombinant polypeptide can be the amount of recombinant polypeptide necessary to treat or inhibit a retinal disorder, stroke, traumatic brain injury, or disorders associated with substance addiction (such as cognitive or neuropsychiatric impairment resulting from substance addiction).

The present disclosure also includes combinations of one or more of the disclosed recombinant polypeptides with one or more other agents useful in the treatment of a disorder. In some examples, the recombinant polypeptides can be administered with effective doses of one or more therapies for inflammatory or autoimmune disorders, including but not limited to non-steroidal anti-inflammatory drugs, corticosteroids, methotrexate, anti-TNF compounds, mycophenolate, aminosalicylates, antibiotics, interferons, glatiramer acetate, antibody therapies (such as rituximab or milatuzumab), or immunosuppressant or immunomodulator compounds. In another example, the recombinant polypeptides can be administered in combination with effective doses of one or more therapies for retinal disorders, including but not limited to, gene therapy, vitamin or mineral supplements (such as vitamins A, C, and/or E, or zinc and/or copper), anti-angiogenic therapy (such as ranibizumab or bevacizumab), photocoagulation, photodynamic therapy, lutein or zeaxanthin, corticosteroids, or immunosuppressants. Appropriate combination therapy for a particular disease can be selected by one of ordinary skill in the art. The term "administration in combination" or "co-administration" refers to both concurrent and sequential administration of the active agents.

EXAMPLES

The following examples are provided to illustrate certain particular features and/or embodiments. These examples should not be construed to limit the disclosure to the particular features or embodiments described.

Example 1

Materials and Methods

Fab, antibodies and other reagents. G4 is a human Fab reactive to the DRα1 domain derived from a human IgG library and was a kind donation from Dr. Yoram Reiter, Technion Israel. Anti-human MOG antibody was purchased from Santa Cruz Biotechnology. CHAPS, T20 and bovine serum albumin were purchased from Sigma-Aldrich. Anti-CD74 antibody was purchased from Everest Biotech. Ultra-Pure™ TRIS was purchased from Invitrogen. Vector pET21d(+) was purchased from Novagen. BL21 (DE3) was purchased from New England Biolabs. IPTG was purchased from Inalco.

DRα1 constructs cloning, expression and purification. The DRα1 construct purification has been reported (Vandenbark et al., *J. Immunol.* 171:127-133, 2003). Briefly, a synthetic DNA fragment containing a sequence encoding the human MOG-35-55 peptide, a flexible linker, and the MHC Class II DRα1 domain from amino acid residues 15 through 97 and a similar synthetic DNA fragment containing the mutation L50Q in the DRα1 domain were cloned into the high level expression vector pET21d(+) (Novagen). These clones were transformed into *E. coli* strain BL21 (DE3) (New England Biolabs), plated onto LB-agar plates containing 50 µg/ml of the antibiotic carbenicillin, and incubated overnight at 37° C. The next day three individual colonies from each clone were selected and grown in LB broth supplemented with the antibiotic to test IPTG-induced production of the protein of interest. After confirmation, a 100 ml overnight culture was prepared and used to inoculate a 4×1 L flask with LB supplemented with the antibiotic. Induction of the target protein synthesis was performed with the addition at the logarithmic growth point of IPTG to a final concentration of 2 mM. The cultures were incubated for an additional 4 hours at 37° C., harvested by centrifugation, and the bacterial paste was frozen at −80° C. until use.

Pellets were resuspended in sonication buffer (50 mM Tris, 300 mM NaCl, 2 mM EDTA pH 8.0) and sonicated to disrupt the cells and release the inclusion bodies. The protein contained in these inclusion bodies were solubilized in a 20 mM Ethanolamine, 6 M Urea, pH 10 buffer overnight at 4° C. with gentle stirring. Purification was achieved by passing the solubilized protein through an anion exchange column and eluting the protein with a NaCl gradient in solubilization buffer. Fractions were collected and analyzed by SDS-PAGE. Those fractions containing the protein of interest were pooled together, dialyzed against 20 mM Tris, pH 8.5, concentrated to 5 mg/ml, and flash frozen and then stored at −80° C. in 1 ml aliquots until use.

Amino acid sequence alignment. All the different Class II α1 domain sequences of interest were retrieved from the NCBI and aligned using the BLAST Two or More sequences from the BLAST website (NIH) and then optimized manually to show relevant regions.

Structural analysis of the proteins by circular dichroism. Proteins were thawed and analyzed by SDS-PAGE (data not shown) prior to testing for their secondary structure content by absorbance of far UV light (180-260 nm) using an AVIV spectrometer. Proteins were greater than 95% pure. One hundred microliters of each of the polypeptides were prepared in 20 mM Tris buffer pH 8.5 at 1 mg/ml concentration and placed in a CD cuvette. Protein was scanned for absorbance in the far UV spectrum from 180 nm to 260 nm through a 0.1 mm light path length taking measurements at every 0.5 nm intervals. A sample containing only 20 mM Tris buffer was also scanned and the signal was subtracted from the protein readings. At least three scans were averaged for each protein and plotted as molar ellipticity.

Binding of DRα1 constructs to CD74 and competition assays. These experiments were performed by ELISA using Maxisorp plates (Nunc) as follows. Prior to the binding and competition experiments the proteins were labeled with Alexa Fluor 488 (Invitrogen) or biotin (Pierce Biotechnology) that targets lysine side chain primary amines. Unconjugated Alexa Fluor 488 or biotin were removed by size exclusion chromatography using a Superdex 75 10/300 column (GE Healthcare). For binding experiments, a recombinant human CD74 (rhCD74) construct was produced (data not shown) and the design, production and purification has already been described (Benedek et al., *Proc. Natl. Acad. Sci. USA* 114:E8421-E8429, 2017). Plates were coated with rhCD74 (C27S) in TBS at a concentration of 0.1 µg/ml for 2 hours at RT or overnight at 4° C. After blocking with 5% BSA in TBS and 0.0125% Tween 20 (T20), DRα1-MOG constructs prepared in blocking buffer with 0.0125% T20 were captured for 3 hours at room temperature followed by detection with streptavidin conjugated to horseradish peroxidase (HRP). Data were loaded onto Prism software and fitted to a one or two binding site equation in order to determine relative affinity.

For competition experiments, ELISA plates were coated with MIF at room temperature at a concentration of 0.5 µg/ml in TBS. Plates were then blocked overnight with 5% BSA in TBS and 0.0125% T20 followed by the addition of a competitive mix containing rhCD74 with serially diluted DRα1 constructs prepared in 5% BSA/TBS plus 0.0125% T20 for 1.5 hours at 25° C. Bound rhCD74 was detected with a monoclonal antibody that specifically recognizes human CD74 in a region away from the putative MIF/D-DT binding site. Absorbance at 450 nm was determined and data were analyzed with Prism, the parameters were calculated with the competition equation included in the software. For competition between DRα1-hMOG-35-55 and P2 peptide (see next section), mouse CD74 was immunoprecipitated from DR*1501 Tg mouse splenocytes and a competition experiment was set. 2.5 µl of P2 peptide were used with increasing concentrations of DRα1-hMOG-35-55 protein. Bound peptide was eluted from the immunoprecipitation with 2% SDS and analyzed in a 16.5% PAG Tris/Tricine. The gel was scanned for FITC and fluorescence was quantified by densitometry. P2 fluorescence vs. DRα1 competitor was plotted and data analyzed with Prism. The relative density values were fit to a One-binding site equation.

Mapping of the CD74-binding epitope on DRα1-hMOG-35-55. A Fab that is able to bind the DRα1-MOG proteins and their parent molecule, RTL1000, with high affinity was previously described (Meza-Romero et al., *J. Immunol.* 192:4164-4173, 2014). However, its binding region on the DRα1 domain has not yet been determined. In order to map the epitope for the G4 Fab, a series of 7 overlapping N-terminus-FITC labeled peptides covering the full length of the DRα1 domain were synthesized. These peptides were tested for their ability to bind In1-immunoprecipitated mouse CD74 from splenocytes and immuno-adsorbed G4 to Protein L beads.

Immunoprecipitation and western blot experiments. After immuno-precipitation, individual peptides were analyzed in a binding experiment for 14-16 hours in 0.1% CHAPS/TEN buffer (50 mM Tris, 2 mM EDTA, 150 mM NaCl, pH 7.4).

Immune complexes were eluted with 50 µl of 2% SDS/ESB (electrophoresis sample buffer) for 20 minutes and then analyzed by electrophoresis in a 10-20% SDS-PAGE under non-reducing conditions. After electrophoresis, the gel was scanned for FITC-labeled peptides. In a parallel experiment immunoprecipitated mouse H2M was used to test the binding of the peptide set. H2M molecules bind the Class II α1 domain but in different regions, therefore they should show a different selectivity for the α1 domain synthetic peptides during binding. We also tested the possibility of G4 and CD74 recognizing the same peptide set since G4 blocks binding of DRα1 constructs to rhCD74. In that regard, G4 Fab was bound to Protein L beads and then either P2 or P7 peptides were applied to the immune complexes. Bound material was eluted as described above, analyzed by electrophoresis and the gel scanned for FITC-labeled material. Western blot experiments were carried out using standard techniques of protein transfer to PVDF (pore size 0.1 µm), followed by blocking with 5% BSA in TBS and 0.05% T20.

ERK1/2 phosphorylation blockade. Two million splenocytes from EAE mice were treated in vitro at 37° C. with 20 mM Tris pH 8.5, 25 µg of DRhQ or DRα1-hMOG-35-55 for 30 minutes. Cells were then spun down and lysed with RIPA buffer supplemented with protease and phosphate inhibitors. Cell lysis was allowed to proceed for 30 minutes on ice and the debris containing nuclei and organelles removed by centrifugation at 14,000 rpm at 4° C. for 10 minutes. Supernatants were collected and subjected to SDS-PAGE in 10-20% gradient gels under reducing conditions. After electrophoresis, proteins were transferred to PVDF and membrane was probed first for p-ERK1/2, stripped and then probed with anti-total ERK1/2 antibody.

EAE induction. C57BL/6 WT male mice between 8 and 12 weeks of age were purchased from the Jackson Laboratory. All procedures were approved and performed according to federal, state, and institutional guidelines. Mice were immunized subcutaneously at four sites on the flanks to distribute 0.2 ml of an emulsion of 200 µg mouse MOG-35-55 peptide and complete Freund's adjuvant containing 400 µg of heat-killed *Mycobacterium tuberculosis* H37RA (Difco) (Meza-Romero et al., *J. Immunol.* 192:4164-4183, 2014). In addition, mice were injected intraperitoneally with Pertussis toxin (Ptx) from List Biological Laboratories on days 0 and 2 post-immunization (75 and 200 ng per mouse, respectively). DRα1-hMOG-35-55, DRbQ, DRα1-mMOG-35-55 and DRmQ proteins (100 µg in 0.1 ml) were injected s.c. daily for 5 days beginning at an EAE score of ≥2.0 and the mice were scored for clinical signs of EAE graded on a six-point scale of combined hindlimb and forelimb paralysis scores as described before (Meza-Romero et al., *J. Immunol.* 192:4164-4183, 2014). Mean EAE scores and SDs for mouse groups were calculated for each day from day 8 through day 27 post-immunization and summed for each mouse by numerically integrating the EAE score curve over the entire experiment (CDI, represents total disease load).

Data analysis. Statistical analyses comparing EAE severity data and equation fitting data for binding and competition results were computed using a Prism software package (GraphPad).

Example 2

Production and Analysis of Modified DRα1 Polypeptides

The production of DRα1-hMOG-35-55, DRα1-mMOG-35-55, DRhQ, and DRmQ proteins were comparable, indicating that the L50Q substitution did not affect the transcription and the expression rate. The protein yield was consistently ~90 to 100 mg/liter of LB broth. Fab G4 was used to detect the purified proteins. In previous studies, it was shown that Fab G4 detected the DRα1 domain in different contexts, including as a stand-alone domain, as part of larger constructs (like the ones described here), or as part of a two-domain recombinant protein (like RTL1000).

An analysis of the alignment of several human Class II α1 domains (FIG. 1) revealed a unique characteristic of the DRα1 domain not shared with other human or mouse class II. This unique feature shows a glutamine (Q) residue at position 18 in most of the sequences used in the alignment (Q18, arrow in FIG. 1; amino acid position 14 in SEQ ID NO: 1). The DRα1 domain, however, has a leucine (L) at position 18. Along with the other peptide-presenting Class II domains, this Q18 residue is also conserved among the non-antigen presenting proteins DMα1 and DOα1. In all the analyzed Class II α1 domain primary sequences and the crystal structures stored in the Protein Data Blank (PDB), this region localizes in the loop between β-strand 1 and β-strand 2 at the N-terminus of the polypeptide pointing outwards of the bulk of the molecule.

Figures 2A, 2B:
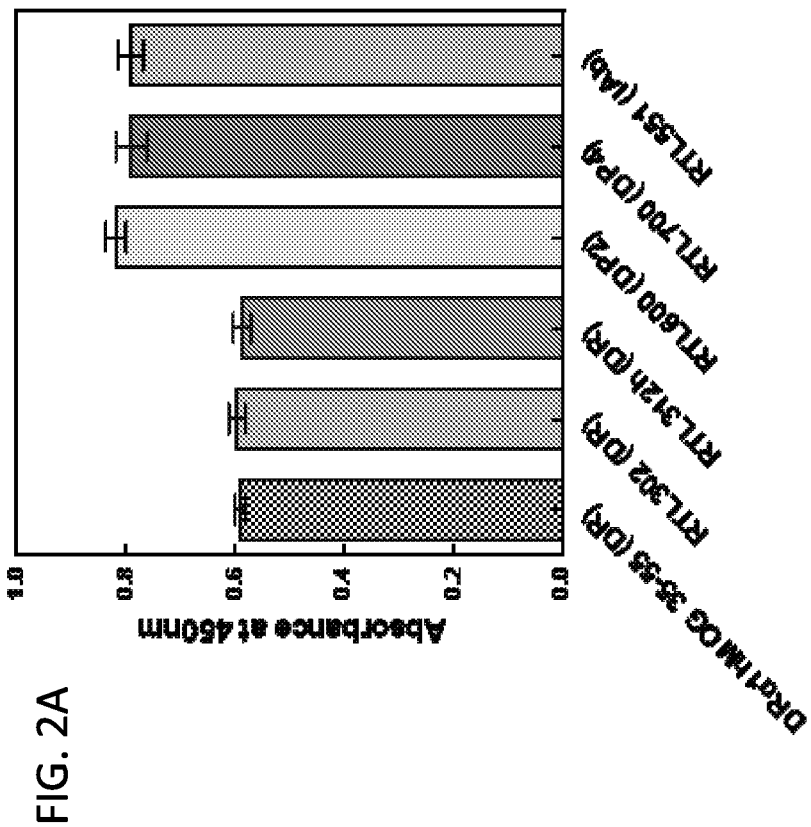
FIGS. 2A and 2B show binding of DRα1-hMOG-35-55, human MHC Class II DR-derived RTL302 (human β1 domain from DRβ1501 followed by the human DRα1 domain; this RTL contains no antigenic peptide and no spacer), human Class II DR-derived RTL312 (human MOG-35-55 peptide, followed by a glycine-serine spacer, a thrombin cleavage site, a glycine-serine spacer, DRβ1 domain from DRβ1501 and a DRα1 domain), human Class II-derived DP2 construct (RTL600; an antigenic peptide, a glycine-serine spacer, a thrombin-cleavage site, a glycine-serine spacer, a DPβ1 domain, and DPα1 domain) and DP4 construct (RTL600; antigenic peptide, a glycine-serine spacer, a thrombin cleavage site, a glycine-serine spacer, the DP4β1 domain, and the DPα1 domain) to CD74. In addition, binding of a mouse MHC Class II-derived RTL551 (mouse MOG-35-55, a glycine-serine spacer, a thrombin cleavage site, a glycine-serine spacer, an IAb (31 domain, and an IAb α1 domain) to coated rhCD74 (C27S) was tested. Binding experiment was carried out using equimolar concentration (250 nm) of each protein ligand (FIG. 2A).

In order to explore the functional role of L18 vs. Q18, binding assays in ELISA experiments were carried out using several previously constructed RTLs from mouse and human origin. FIG. 2A shows that those polypeptides which have Q18 (DP2, DP4, and mouse derived RTL551 (IAb)) displayed greater binding activity to rhCD74 in ELISA assays than constructs with L18. The mutant polypeptides were produced (sequences shown in FIG. 2B) to investigate whether L18 vs. Q18 (position 50 in the DRα1-MOG-35-55 constructs) might have different binding affinities for the CD74 receptor.

Human Fab G4 (that recognizes the DRα1 domain) was used as a tool to determine whether the L50Q substitution affected the immunological recognition of the DRα1 constructs. The Fab G4 cross-reacted with the DRhQ mutant in the same manner as it did with the DRα1-hMOG-35-55 as well as the DRα1-mMOG-35-55 (FIG. 3A). In order to compare the secondary structure content of the DRhQ and DRα1-MOG-35-55 proteins side by side, far UV scanning of the protein in a circular dichroism spectrometer was carried out (FIG. 3B). It was shown in previous studies that DRα1-hMOG-35-55 contains a significant amount of alpha-helix and beta sheet secondary structures (Meza-Romero et al., *J. Immunol.* 192:4164-4183, 2014). All the molecules showed a high positive absorbance at 190 nm, the main feature indicative of an α-helix element, and a negative absorbance at 215 nm indicating the presence of β-sheet secondary structure. Overall these results show that the three proteins are structurally similar, suggesting that the replacement of a Leucine (L) for a Glutamine (Q) in the β-sheet platform of the constructs altered only minimally the alpha-helix content but did not alter the amount of beta-sheet structure at the bottom of the molecule.

Seven overlapping peptides spanning the whole length of the DRα1 protein were designed (FIG. 4A). These peptides contained a FITC moiety at the N-terminus of the amino acid sequence in order to be detected by fluorescence scanning. Of these, P1 had to be modified due to a solubility issue of the full length peptide and a second peptide (P6) could not be synthesized. The peptides were used, individually and as a pool, to bind immuno-precipitated CD74 from mouse splenocytes. As a first approach a cocktail of all peptides was added simultaneously to Protein A/G beads containing ln1-immunoprecipitated CD74. As is shown in FIG. 4B, only two peptides, P2, and P5 to a minor extent, bound to immunoprecipitated mouse CD74. To confirm this, individual peptides were added the Protein A/G-ln1-CD74 complexes under the same conditions. As shown in FIG. 4B, only P2 and P5 peptides bound clearly to mouse CD74. P2 exhibited stronger binding, while P5 had lower affinity.

In order to test the usefulness of this strategy the experiment was also run with immuno-precipitated H2M. It was hypothesized that a different peptide (or set of peptides) would bind to H2M. As seen in FIG. 4C a different set of the overlapping peptides bound to this protein, validating the results of the previous experiment. This later experiment showed that P7 peptide strongly bound immunoprecipitated H2M and to a minor extent P4 (FIG. 4C). This result is consistent with the published crystal structure of the DR/DM complex (Pos et al., Cell 151:1557-1568, 2012). The interface of these two molecules is dominated by the alpha chains of DM and DR. DM binds to a lateral surface of the DRα1 domain away from the N-terminus of the DRα1 region and close to the peptide binding groove without contacting the DRβ1 domain.

In previous publications, it has been demonstrated that the G4 Fab was effective to block DRα1 construct binding to CD74 (Meza-Romero et al., *J. Immunol.* 192:4164-4173, 2014). Therefore, an experiment aimed to determine whether P2 also interacted with Protein L bound G4 Fab and compare the binding to immunoprecipitated CD74 was carried out. Potentially, the P7 peptide would not bind to G4 or CD74. As expected only the P2 peptide was able to bind G4, demonstrating that G4 and CD74 have the same binding site on DRα1 polypeptides (FIG. 5A). FIG. 5B shows a schematic view of the DRα1 domain with the P2 peptide location. To confirm that the P2 peptide was associated with the interface to bind CD74, a competition experiment was carried out to determine whether DRα1-hMOG-35-55 and P2 peptide compete with each other to bind mCD74. The results showed that DRα1-hMOG-35-55 was able to outcompete the binding of the FITC-labeled P2 peptide to immunoprecipitated CD74 with a relative affinity ($K_D$) of 750 nM (FIG. 5C).

DRα1-MOGs, including DRα1-hMOG-35-55, DRhQ, DRα1-mMOG-35-55, and DRmQ were evaluated for binding to their receptor. A recombinant human CD74(C27S) was coated onto the ELISA plate and then, following blocking, DRα1 constructs were captured for 1 to 1.5 hours at RT and detected with an anti-MOG antibody. The results were entered into the Prism software and the $K_D$ calculated fitting the curve to a one-site specific binding equation. As shown in FIG. 6A and in Table 2, these results indicate that the replacement of leucine with glutamine at position 50 of the DRα1 constructs (or position 18 in the alignment, or 14 in SEQ ID NO: 1) increased the binding capacity of the mutant proteins.

TABLE 2

Binding affinities for CD74

Binding affinities for DRα1-hMOG-35-55 and DRhQ for CD74

|  | DRhQ | DRα1-hMOG-35-55 |
|---|---|---|
| $K_D$ | 0.09109 | 0.7015 |
| 95% CI | 0.07146 to 0.1161 | 0.1304 to 1.774 |
| R square | 0.999 | 0.996 |

TABLE 2-continued

Binding affinities for CD74

Competition of DRα1-MOG constructs vs MIF to bind CD74

|  | DRhQ | DRα1-hMOG-35-55 | DRmQ | DRα1-mMOG-35-55 |
|---|---|---|---|---|
| IC50 | 0.2978 | 1.639 | 0.8279 | 0.9369 |
| 95% CI | 0.1821 to 0.4870 | 0.9047 to 2.968 | 0.4599 to 1.490 | 0.4783 to 1.835 |
| R square | 0.9691 | 0.9601 | 0.9658 | 0.9461 |

The DRhQ mutant bound with between 8- to 10-fold higher affinity to the receptor when compared to the counterpart wild type version of the constructs (see Table 2 with $K_D$). This confirms that the region containing L50 is likely to be part of the binding site of DRα constructs to CD74, as suggested by the docking model of the DRα/CD74 interaction (Meza-Romero et al., *Metab. Brain Dis.* 31:249-255, 2016; Wingerchuk et al., *Mayo Clin. Proc.* 89:225-240, 2014) and the experiments with the P2 peptide discussed above. Competition assays were consistent with the direct binding results (FIG. 6B). In the competition experiments DRhQ showed greater ability, 8- to 10-fold higher, to outcompete MIF for its binding to CD74 than the DRα1-hMOG-35-55 (DRhQ $IC_{50}$=0.28 μM vs DRα1-hMOG-35-55 $IC_{50}$=1.6 μM), arguing in favor a more direct role that this region contributes to the binding interaction. On the other hand, DRα1-mMOG-35-55 and its derivative DRmQ showed no significant differences between them and basically displayed an intermediate competitive activity when compared to DRhQ.

As shown in FIG. 7A, treatment of C57BL/6 male mice with the DRhQ construct significantly reduced the severity of ongoing EAE compared with the native L50 containing DRα1-hMOG-35-55 construct. In contrast, treatment with the DRmQ construct, which did not differ in its ability to block MIF binding to CD74 (see above), did not differ in its treatment effect on EAE compared with the L50 containing DRα1-mMOG-35-55 construct (FIG. 7B).

Studies have shown that MIF is the main pro-inflammatory cytokine driving the ERK1/2 phosphorylation through the interaction with CD74/CD44 on the cell surface (Leng et al., *J. Exp. Med.* 197:1467-1476, 2003). Splenocytes harvested from EAE mice showed upregulated levels of p-ERK1/2, indicating an ongoing active signaling cascade associated with the inflammatory process. Upon treatment with the DRα1-MOG constructs this phosphorylation was downregulated in vitro after a 30 minute incubation. This suggests that treating splenocytes from an animal with an ongoing inflammatory reaction with the constructs resulted in down regulation of ERK1/2 phosphorylation (FIG. 8).

In the crystal structures of several human and mouse Class II molecules deposited in the Protein Data Bank, the Q amino acid residue locates at the end of the β-strand 1 in the loop between the β-strand 1 and the β-strand 2 at the N-terminus of the domain (FIGS. 9A and 9B). In fact, this loop has been implicated in the binding of the TSST-1 toxin to the α1 domain of class II (Karp et al., *Nature* 346:474-476, 1990; Kim et al., *Science* 266:1870-1874, 1994) and the association between Class II and the invariant chain (Ii, CD74) prevents binding of TSST to Class II (Karp et al., *Proc. Natl. Acad. Sci. USA* 89:9657-9661, 1992), suggesting a potential shared or overlapping epitope. Using a protein-protein docking algorithm, we predicted the existence of an interface between CD74 and DRα1-hMOG-35-55 (Meza-Romero et al., *Metab. Brain Dis.* 31:249-255, 2016; Wingerchuk et al., *Mayo Clin. Proc.* 89:225-240, 2014) and defined the amino acid residues F48, L50, P52, D53 and S55 in the construct (F12, L14, P16, D17 and S19, in FIG. 9A) as important components of this interface. We therefore introduced the Q mutation into the DRα1-hMOG-35-55 and the DRα1-mMOG-35-55 to create the DRhQ and the DRmQ variants, respectively. From the immunological and biophysical standpoints, these novel mutants are indistinguishable from their parent molecules. Both proteins show the same level and quality of cross-reaction to the Fab G4, suggesting that the epitope has not been structurally modified (FIG. 3A). Likewise, both constructs show identical profiles by circular dichroism spectrometry indicating that the secondary structure has been preserved in the mutants DRhQ (FIG. 3B) and DRmQ (not shown).

Earlier experimental studies suggested that in addition to DRα1-MOG-35-55 (Benedek et al., *Eur. J. Immunol.* 43:1309-1321, 2013), RTL1000 was also able to bind to and block MIF binding to CD74 (Benedek et al., *Proc. Natl. Acad. Sci. USA* 114:E8421-E8429, 2017). By using a set of overlapping peptides spanning the DRα1 domain amino acid sequence, the major binding site was narrowed down to the N-terminus of the DRα1 domain (FIGS. 4A and 4B), as predicted by the docking algorithm (Meza-Romero et al., *Cytokine* 88:62-70, 2016; Meza-Romero et al., *Metab. Brain Dis.* 31:249-255, 2016). All these amino acid residues make up the core of the P2 peptide that was shown to bind to immunoprecipitated mouse CD74 and to Fab G4 (FIG. 5A). In addition, DRα1-hMOG-35-55 outcompeted the P2 peptide to bind to immunopurified mouse CD74 (FIG. 5C) indicating that both ligands bind to the receptor in the same region. A close inspection of crystal structures of several mouse and human MHC Class II molecules showed that these residues are located in the loop between the β1 and β2 strands at the N-terminus of the α1 domain. According to our docking model, the residues within this loop make close contact with residues on CD74 (FIG. 9A).

We also tested this novel variant for its binding to a recombinant version of human CD74 and its activity to prevent or outcompete MIF from binding to their receptor. Our results indicate that the Q-harboring variant showed a $K_D$ 8-10-fold higher affinity for CD74 in direct binding ELISA assays, in sharp contrast to the parent molecule, suggesting that the Q at this position favorably influenced the interaction (FIG. 6A, Table 2). Accordingly, DRhQ showed more competitive activity versus MIF to bind the CD74 receptor with an 8 to 10-fold higher $IC_{50}$ (FIG. 6B, Table 2). This higher affinity evaluated by direct binding and by competition experiments was reflected in the potency of the drug to treat EAE in experimental animals. As shown in FIGS. 7A and 7B, these constructs were able to significantly reduce the disease scores in mice compared to a lack of a treatment effect with DRα1-hMOG-35-55 with this level of disease severity. These experiments demonstrate that splenocytes harvested from EAE mice showed upregulated levels of p-ERK1/2 indicating an ongoing active signaling cascade associated with the inflammatory process and that this phosphorylation of ERK1/2 can be down regulated by DRhQ treatment in vitro (FIG. 8).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A recombinant polypeptide comprising a DRα1 domain comprising a glutamine residue at a position corresponding to amino acid position 14 of SEQ ID NO: 1.

2. The recombinant polypeptide of claim 1, wherein the DRα1 domain is a human DRα1 domain.

3. The recombinant polypeptide of claim 1, comprising an amino acid sequence with at least 90% sequence identity to SEQ ID NO: 1.

4. The recombinant polypeptide of claim 3, comprising the amino acid sequence of SEQ ID NO: 1.

5. The recombinant polypeptide of claim 4, consisting of the amino acid sequence of SEQ ID NO: 1.

6. The recombinant polypeptide of claim 1, further comprising an antigenic peptide.

7. The recombinant polypeptide of claim 6, further comprising a linker.

8. The recombinant polypeptide of claim 7, wherein the linker comprises a peptide linker or a chemical crosslinker.

9. The recombinant polypeptide of claim 7, wherein the linker comprises a first glycine-serine spacer, a thrombin cleavage site and a second glycine-serine spacer.

10. The recombinant polypeptide of claim 6, wherein the antigenic peptide is MOG-35-55 (oligodendrocyte glycoprotein).

11. The recombinant polypeptide of claim 10, wherein the MOG-35-55 is human or mouse MOG-35-55.

12. The recombinant polypeptide of claim 10, wherein the recombinant polypeptide comprises or consists of SEQ ID NO: 2 or SEQ ID NO: 3.

13. A nucleic acid molecule encoding the recombinant polypeptide of claim 1.

14. An expression construct comprising the nucleic acid of claim 13.

15. A cell line comprising the expression construct of claim 14.

16. A pharmaceutical composition comprising:
an effective amount of the recombinant polypeptide of claim 1; and
a pharmaceutically acceptable carrier.

17. The pharmaceutical composition of claim 16, wherein the composition comprises at least 5 mg/kg of the recombinant polypeptide.

18. A method of treating an inflammatory disorder comprising administering an effective amount of the pharmaceutical composition of claim 16 to a subject with the inflammatory disorder.

19. The method of claim 18, wherein the inflammatory disorder is multiple sclerosis or experimental autoimmune encephalopathy (EAE).

20. A pharmaceutical composition comprising:
an effective amount of the nucleic acid molecule of claim 13; and
a pharmaceutically acceptable carrier.

* * * * *

SEQUENCE LISTING

<160> NUMBER OF SEQ ID NOS: 64

<210> SEQ ID NO 1
<211> LENGTH: 84
<212> TYPE: PRT
<213> ORGANISM: Artificial Sequence
<220> FEATURE:
<223> OTHER INFORMATION: Modified DRalpha1 polypeptide

<400> SEQUENCE: 1

Ile Lys Glu Glu His Val Ile Ile Gln Ala Glu Phe Tyr Gln Asn Pro
1               5                   10                  15

Asp Gln Ser Gly Glu Phe Met Phe Asp Phe Asp Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

Pro Ile Thr Asn

<210> SEQ ID NO 2
<211> LENGTH: 120
<212> TYPE: PRT
<213> ORGANISM: Artificial Sequence
<220> FEATURE:
<223> OTHER INFORMATION: DRhQ polypeptide

<400> SEQUENCE: 2

Met Glu Val Gly Trp Tyr Arg Pro Pro Phe Ser Arg Val Val His Leu
1               5                   10                  15

Tyr Arg Asn Gly Lys Gly Gly Gly Ser Leu Val Pro Arg Gly Ser
            20                  25                  30

Gly Gly Gly Gly Ile Lys Glu His Val Ile Ile Gln Ala Glu Phe
            35                  40                  45

Tyr Gln Asn Pro Asp Gln Ser Gly Glu Phe Met Phe Asp Phe Asp Gly
50                  55                  60

Asp Glu Ile Phe His Val Asp Met Ala Lys Lys Glu Thr Val Trp Arg
65                  70                  75                  80

Leu Glu Glu Phe Gly Arg Phe Ala Ser Phe Glu Ala Gln Gly Ala Leu
                85                  90                  95

Ala Asn Ile Ala Val Asp Lys Ala Asn Leu Glu Ile Met Thr Lys Arg
            100                 105                 110

Ser Asn Tyr Thr Pro Ile Thr Asn
        115                 120

<210> SEQ ID NO 3
<211> LENGTH: 120
<212> TYPE: PRT
<213> ORGANISM: Artificial Sequence
<220> FEATURE:
<223> OTHER INFORMATION: DRmQ polypeptide

<400> SEQUENCE: 3

Met Glu Val Gly Trp Tyr Arg Ser Pro Phe Ser Arg Val Val His Leu
1               5                   10                  15

Tyr Arg Asn Gly Lys Gly Gly Gly Ser Leu Val Pro Arg Gly Ser
            20                  25                  30

Gly Gly Gly Gly Ile Lys Glu Glu His Val Ile Ile Gln Ala Glu Phe
            35                  40                  45

Tyr Gln Asn Pro Asp Gln Ser Gly Glu Phe Met Phe Asp Phe Asp Gly
50                  55                  60

Asp Glu Ile Phe His Val Asp Met Ala Lys Lys Glu Thr Val Trp Arg
65                  70                  75                  80

Leu Glu Glu Phe Gly Arg Phe Ala Ser Phe Glu Ala Gln Gly Ala Leu
                85                  90                  95

Ala Asn Ile Ala Val Asp Lys Ala Asn Leu Glu Ile Met Thr Lys Arg
            100                 105                 110

Ser Asn Tyr Thr Pro Ile Thr Asn
        115                 120

<210> SEQ ID NO 4
<211> LENGTH: 242
<212> TYPE: DNA
<213> ORGANISM: Artificial Sequence
<220> FEATURE:
<223> OTHER INFORMATION: Nucleiic acid encoding modified DRalpha1
      polypeptide

<400> SEQUENCE: 4
atcaaagaag aacatgtgat catccaggcc gagttctatc agaatcctga ccaatcaggc      60
gagtttatgt ttgactttga tggtgatgag attttccatg tggatatggc aaagaaggag     120
acggtctggc ggcttgaaga atttggacga tttgccagct ttgaggctca aggtgcattg     180
gccaacatag ctgtggacaa agccaacttg gaaatcatga caaagcgctc caactatact     240

-continued cc                                                              242

<210> SEQ ID NO 5
<211> LENGTH: 363
<212> TYPE: DNA
<213> ORGANISM: Artificial Sequence
<220> FEATURE:
<223> OTHER INFORMATION: Nucleic acid encoding DRhQ

<400> SEQUENCE: 5
atggaagttg gttggtaccg tccgccgttc tcccgtgttg ttcacctgta ccgtaacggt      60
aaaggaggtg gaggctcact agtgccccga ggctctggag gtggaggcat caaagaagaa     120
catgtgatca tccaggccga gttctatcag aatcctgacc aatcaggcga gtttatgttt     180
gactttgatg gtgatgagat tttccatgtg gatatggcaa agaaggagac ggtctggcgg     240
cttgaagaat ttggacgatt tgccagcttt gaggctcaag gtgcattggc caacatagct     300
gtggacaaag ccaacttgga aatcatgaca aagcgctcca actatactcc gatcaccaat     360
taa                                                                    363

<210> SEQ ID NO 6
<211> LENGTH: 363
<212> TYPE: DNA
<213> ORGANISM: Artificial Sequence
<220> FEATURE:
<223> OTHER INFORMATION: Nucleic acid encoding DRmQ

<400> SEQUENCE: 6
atggaagttg gttggtaccg ttccccgttc tcccgtgttg ttcacctgta ccgtaacggt      60
aaaggaggtg gaggctcact agtgccccga ggctctggag gtggaggcat caaagaagaa     120
catgtgatca tccaggccga gttctatcaa aatcctgacc aatcaggcga gtttatgttt     180
gactttgatg gtgatgagat tttccatgtg gatatggcaa agaaggagac ggtctggcgg     240
cttgaagaat ttggacgatt tgccagcttt gaggctcaag gtgcattggc caacatagct     300
gtggacaaag ccaacttgga aatcatgaca aagcgctcca actatactcc gatcaccaat     360
taa                                                                    363

<210> SEQ ID NO 7
<211> LENGTH: 59
<212> TYPE: PRT
<213> ORGANISM: Artificial Sequence
<220> FEATURE:
<223> OTHER INFORMATION: human DM1 alpha 1 domain

<400> SEQUENCE: 7

Trp Pro Asp Asp Leu Gln Asn His Thr Phe Leu His Thr Val Tyr Cys
1               5                   10                  15

Gln Asp Gly Ser Pro Ser Val Gly Leu Ser Glu Ala Tyr Asp Glu Asp
            20                  25                  30

Gln Leu Phe Phe Phe Asp Phe Ser Gln Asn Thr Arg Val Pro Arg Leu
        35                  40                  45

Pro Glu Phe Ala Asp Trp Ala Gln Glu Gln Gly
    50                  55

<210> SEQ ID NO 8
<211> LENGTH: 60
<212> TYPE: PRT
<213> ORGANISM: Artificial Sequence
<220> FEATURE:
<223> OTHER INFORMATION: Human DO1 alpha1 domain

```
<400> SEQUENCE: 8

Ala Gly Ala Thr Lys Ala Asp His Met Gly Ser Tyr Gly Pro Ala Phe
1               5                   10                  15

Tyr Gln Ser Tyr Gly Ala Ser Gly Gln Phe Thr His Glu Phe Asp Glu
            20                  25                  30

Glu Gln Leu Phe Ser Val Asp Leu Lys Lys Ser Glu Ala Val Trp Arg
        35                  40                  45

Leu Pro Glu Phe Gly Asp Phe Ala Arg Phe Asp Pro
    50                  55                  60

<210> SEQ ID NO 9
<211> LENGTH: 60
<212> TYPE: PRT
<213> ORGANISM: Artificial Sequence
<220> FEATURE:
<223> OTHER INFORMATION: Human DQ1 alpha1 domain

<400> SEQUENCE: 9

Gly Glu Asp Ile Val Ala Asp His Val Ala Ser Cys Gly Val Asn Leu
1               5                   10                  15

Tyr Gln Phe Tyr Gly Pro Ser Gly Gln Tyr Thr His Glu Phe Asp Gly
            20                  25                  30

Asp Glu Gln Phe Tyr Val Asp Leu Glu Arg Lys Glu Thr Ala Trp Arg
        35                  40                  45

Trp Pro Glu Phe Ser Lys Phe Gly Gly Phe Asp Pro
    50                  55                  60

<210> SEQ ID NO 10
<211> LENGTH: 60
<212> TYPE: PRT
<213> ORGANISM: Artificial Sequence
<220> FEATURE:
<223> OTHER INFORMATION: Human DQ2 alpha1 domain

<400> SEQUENCE: 10

Gly Glu Asp Ile Val Ala Asp His Val Ala Ser Tyr Gly Val Asn Phe
1               5                   10                  15

Tyr Gln Ser His Gly Pro Ser Gly Gln Tyr Thr His Glu Phe Asp Gly
            20                  25                  30

Asp Glu Glu Phe Tyr Val Asp Leu Glu Thr Lys Glu Thr Val Trp Gln
        35                  40                  45

Leu Pro Met Phe Ser Lys Phe Ile Ser Phe Asp Pro
    50                  55                  60

<210> SEQ ID NO 11
<211> LENGTH: 59
<212> TYPE: PRT
<213> ORGANISM: Artificial Sequence
<220> FEATURE:
<223> OTHER INFORMATION: Human DP4 alpha1 domain

<400> SEQUENCE: 11

Arg Arg Val Ile Lys Ala Asp His Val Ser Thr Tyr Ala Ala Phe Val
1               5                   10                  15

Gln Thr His Arg Pro Thr Gly Glu Phe Met Phe Glu Phe Asp Glu Asp
            20                  25                  30

Glu Met Phe Tyr Val Asp Leu Asp Lys Lys Glu Thr Val Trp His Leu
        35                  40                  45

Glu Glu Phe Gly Gln Ala Phe Ser Phe Glu Ala
```

<210> SEQ ID NO 12
<211> LENGTH: 59
<212> TYPE: PRT
<213> ORGANISM: Artificial Sequence
<220> FEATURE:
<223> OTHER INFORMATION: Human DP2 alpha1 domain

<400> SEQUENCE: 12

Ala Gly Ala Ile Lys Ala Asp His Val Ser Thr Tyr Ala Ala Phe Val
1               5                   10                  15

Gln Thr His Arg Pro Thr Gly Glu Phe Met Phe Glu Phe Asp Glu Asp
                20                  25                  30

Glu Met Phe Tyr Val Asp Leu Asp Lys Lys Glu Thr Val Trp His Leu
            35                  40                  45

Glu Glu Phe Gly Gln Ala Phe Ser Phe Glu Ala
        50                  55

<210> SEQ ID NO 13
<211> LENGTH: 59
<212> TYPE: PRT
<213> ORGANISM: Artificial Sequence
<220> FEATURE:
<223> OTHER INFORMATION: Human DR1 alpha1 domain

<400> SEQUENCE: 13

Ser Trp Ala Ile Lys Glu Glu His Val Ile Ile Gln Ala Glu Phe Tyr
1               5                   10                  15

Leu Asn Pro Asp Gln Ser Gly Glu Phe Met Phe Asp Phe Asp Gly Asp
                20                  25                  30

Glu Ile Phe His Val Asp Met Ala Lys Lys Glu Thr Val Trp Arg Leu
            35                  40                  45

Glu Glu Phe Gly Arg Phe Ala Ser Phe Glu Ala
        50                  55

<210> SEQ ID NO 14
<211> LENGTH: 60
<212> TYPE: PRT
<213> ORGANISM: Artificial Sequence
<220> FEATURE:
<223> OTHER INFORMATION: Mouse IAk alpha 1 domain

<400> SEQUENCE: 14

Glu Asp Asp Ile Glu Ala Asp His Val Gly Ser Tyr Gly Ile Thr Val
1               5                   10                  15

Tyr Gln Ser Pro Gly Asp Ile Gly Gln Tyr Thr Phe Glu Phe Asp Gly
                20                  25                  30

Asp Glu Leu Phe Tyr Val Asp Leu Asp Lys Lys Glu Thr Val Trp Met
            35                  40                  45

Leu Pro Glu Phe Ala Gln Leu Arg Arg Phe Glu Pro
        50                  55                  60

<210> SEQ ID NO 15
<211> LENGTH: 60
<212> TYPE: PRT
<213> ORGANISM: Artificial Sequence
<220> FEATURE:
<223> OTHER INFORMATION: Mouse IAd alpha1 domain

<400> SEQUENCE: 15

Glu Asp Asp Ile Glu Ala Asp His Val Gly Phe Tyr Gly Thr Thr Val

```
                 1               5                  10                  15
Tyr Gln Ser Pro Gly Asp Ile Gly Gln Tyr Thr His Glu Phe Asp Gly
                20                  25                  30

Asp Glu Leu Phe Tyr Val Asp Leu Asp Lys Lys Lys Thr Val Trp Arg
        35                  40                  45

Leu Pro Glu Phe Gly Gln Leu Ile Leu Phe Glu Pro
        50                  55                  60

<210> SEQ ID NO 16
<211> LENGTH: 60
<212> TYPE: PRT
<213> ORGANISM: Artificial Sequence
<220> FEATURE:
<223> OTHER INFORMATION: Mouse IAb alpha1 domain

<400> SEQUENCE: 16

Glu Asp Asp Ile Glu Ala Asp His Val Gly Thr Tyr Gly Thr Ser Val
1               5                   10                  15

Tyr Gln Ser Pro Gly Asp Ile Gly Gln Tyr Thr Phe Glu Phe Asp Gly
                20                  25                  30

Asp Glu Leu Phe Tyr Val Asp Leu Asp Lys Lys Lys Thr Val Trp Arg
        35                  40                  45

Leu Pro Glu Phe Gly Gln Leu Ala Ser Phe Asp Pro
        50                  55                  60

<210> SEQ ID NO 17
<211> LENGTH: 60
<212> TYPE: PRT
<213> ORGANISM: Artificial Sequence
<220> FEATURE:
<223> OTHER INFORMATION: Mouse IAf alpha1 domain

<400> SEQUENCE: 17

Glu Asp Asp Ile Glu Ala Asp His Val Gly Phe Tyr Gly Ile Ser Val
1               5                   10                  15

Tyr Gln Ser Pro Gly Asp Ile Gly Gln Tyr Thr Phe Glu Phe Asp Gly
                20                  25                  30

Asp Glu Trp Phe Tyr Val Asp Leu Asp Lys Lys Glu Thr Val Trp Arg
        35                  40                  45

Leu Pro Glu Phe Gly Gln Leu Thr Ser Phe Asp Pro
        50                  55                  60

<210> SEQ ID NO 18
<211> LENGTH: 60
<212> TYPE: PRT
<213> ORGANISM: Artificial Sequence
<220> FEATURE:
<223> OTHER INFORMATION: Mouse IAu alpha1 domain

<400> SEQUENCE: 18

Glu Asp Asp Ile Glu Ala Asp His Val Gly Ser Tyr Gly Ile Val Val
1               5                   10                  15

Tyr Gln Ser Pro Gly Asp Ile Gly Gln Tyr Thr Phe Glu Phe Asp Gly
                20                  25                  30

Asp Glu Leu Phe Tyr Val Asp Leu Asp Lys Lys Glu Thr Ile Trp Met
        35                  40                  45

Leu Pro Glu Phe Ala Gln Leu Arg Ser Phe Asp Pro
        50                  55                  60

<210> SEQ ID NO 19
```

<211> LENGTH: 60
<212> TYPE: PRT
<213> ORGANISM: Artificial Sequence
<220> FEATURE:
<223> OTHER INFORMATION: Mouse IA1 alpha1 domain

<400> SEQUENCE: 19

Glu Asp Asp Ile Glu Ala Asp His Val Gly Ser Tyr Gly Ile Val Val
1               5                   10                  15

Tyr Gln Ser Pro Gly Asp Ile Gly Gln Tyr Thr His Glu Phe Asp Gly
                20                  25                  30

Asp Glu Trp Phe Tyr Val Asp Leu Asp Lys Lys Glu Thr Val Trp Met
            35                  40                  45

Leu Pro Glu Phe Gly Gln Leu Thr Ser Phe Asp Pro
        50                  55                  60

<210> SEQ ID NO 20
<211> LENGTH: 59
<212> TYPE: PRT
<213> ORGANISM: Artificial Sequence
<220> FEATURE:
<223> OTHER INFORMATION: Partial DRalpha1-hMOG-35-55 sequence

<400> SEQUENCE: 20

Met Glu Val Gly Trp Tyr Arg Pro Pro Phe Ser Arg Val Val His Leu
1               5                   10                  15

Tyr Arg Asn Gly Lys Gly Gly Gly Ser Leu Val Pro Arg Gly Ser
                20                  25                  30

Gly Gly Gly Gly Ile Lys Glu Glu His Val Ile Ile Gln Ala Glu Phe
            35                  40                  45

Tyr Leu Asn Pro Asp Gln Ser Gly Glu Phe Met
        50                  55

<210> SEQ ID NO 21
<211> LENGTH: 59
<212> TYPE: PRT
<213> ORGANISM: Artificial Sequence
<220> FEATURE:
<223> OTHER INFORMATION: Partial DRhQ sequence

<400> SEQUENCE: 21

Met Glu Val Gly Trp Tyr Arg Pro Pro Phe Ser Arg Val Val His Leu
1               5                   10                  15

Tyr Arg Asn Gly Lys Gly Gly Gly Ser Leu Val Pro Arg Gly Ser
                20                  25                  30

Gly Gly Gly Gly Ile Lys Glu Glu His Val Ile Ile Gln Ala Glu Phe
            35                  40                  45

Tyr Gln Asn Pro Asp Gln Ser Gly Glu Phe Met
        50                  55

<210> SEQ ID NO 22
<211> LENGTH: 59
<212> TYPE: PRT
<213> ORGANISM: Artificial Sequence
<220> FEATURE:
<223> OTHER INFORMATION: Partial DRalpha1-mMOG-35-55 sequence

<400> SEQUENCE: 22

Met Glu Val Gly Trp Tyr Arg Pro Ser Phe Ser Arg Val Val His Leu
1               5                   10                  15

Tyr Arg Asn Gly Lys Gly Gly Gly Gly Ser Leu Val Pro Arg Gly Ser
                20                  25                  30

```
Gly Gly Gly Gly Ile Lys Glu Glu His Val Ile Ile Gln Ala Glu Phe
            35                  40                  45

Tyr Leu Asn Pro Asp Gln Ser Gly Glu Phe Met
    50                  55

<210> SEQ ID NO 23
<211> LENGTH: 59
<212> TYPE: PRT
<213> ORGANISM: Artificial Sequence
<220> FEATURE:
<223> OTHER INFORMATION: Partial DRmQ sequence

<400> SEQUENCE: 23

Met Glu Val Gly Trp Tyr Arg Pro Ser Phe Ser Arg Val Val His Leu
1               5                   10                  15

Tyr Arg Asn Gly Lys Gly Gly Gly Ser Leu Val Pro Arg Gly Ser
            20                  25                  30

Gly Gly Gly Gly Ile Lys Glu Glu His Val Ile Ile Gln Ala Glu Phe
            35                  40                  45

Tyr Gln Asn Pro Asp Gln Ser Gly Glu Phe Met
    50                  55

<210> SEQ ID NO 24
<211> LENGTH: 86
<212> TYPE: PRT
<213> ORGANISM: Artificial Sequence
<220> FEATURE:
<223> OTHER INFORMATION: Modified DRalpha1

<400> SEQUENCE: 24

Met Gly Ile Lys Glu Glu His Val Ile Ile Gln Ala Glu Phe Tyr Gln
1               5                   10                  15

Asn Pro Asp Gln Ser Gly Glu Phe Met Phe Asp Phe Asp Gly Asp Glu
            20                  25                  30

Ile Phe His Val Asp Met Ala Lys Lys Glu Thr Val Trp Arg Leu Glu
            35                  40                  45

Glu Phe Gly Arg Phe Ala Ser Phe Glu Ala Gln Gly Ala Leu Ala Asn
    50                  55                  60

Ile Ala Val Asp Lys Ala Asn Leu Glu Ile Met Thr Lys Arg Ser Asn
65                  70                  75                  80

Tyr Thr Pro Ile Thr Asn
            85

<210> SEQ ID NO 25
<211> LENGTH: 30
<212> TYPE: PRT
<213> ORGANISM: Artificial Sequence
<220> FEATURE:
<223> OTHER INFORMATION: Peptide P1

<400> SEQUENCE: 25

Met Gly Ile Lys Glu Glu His Val Ile Ile Gln Ala Glu Phe Tyr Gln
1               5                   10                  15

Asn Pro Asp Gln Ser Gly Glu Phe Met Phe Asp Phe Asp Gly
            20                  25                  30

<210> SEQ ID NO 26
<211> LENGTH: 30
<212> TYPE: PRT
<213> ORGANISM: Artificial Sequence
<220> FEATURE:
```

<223> OTHER INFORMATION: Peptide P2

<400> SEQUENCE: 26

Gln Ala Glu Phe Tyr Gln Asn Pro Asp Gln Ser Gly Glu Phe Met Phe
1               5                   10                  15

Asp Phe Asp Gly Asp Glu Ile Phe His Val Asp Met Ala Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Peptide P3

<400> SEQUENCE: 27

Ser Gly Glu Phe Met Phe Asp Phe Asp Gly Asp Glu Ile Phe His Val
1               5                   10                  15

Asp Met Ala Lys Lys Glu Thr Val Trp Arg Leu Glu Glu Phe
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Peptide P4

<400> SEQUENCE: 28

Asp Glu Ile Phe His Val Asp Met Ala Lys Lys Glu Thr Val Trp Arg
1               5                   10                  15

Leu Glu Glu Phe Gly Arg Phe Ala Ser Phe Glu Ala Gln Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Peptide P5

<400> SEQUENCE: 29

Lys Glu Thr Val Trp Arg Leu Glu Glu Phe Gly Arg Phe Ala Ser Phe
1               5                   10                  15

Glu Ala Gln Gly Ala Leu Ala Asn Ile Ala Val Asp Lys Ala
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Peptide P6

<400> SEQUENCE: 30

Gly Arg Phe Ala Ser Phe Glu Ala Gln Gly Ala Leu Ala Asn Ile Ala
1               5                   10                  15

Val Asp Lys Ala Asn Leu Glu Ile Met Thr Lys Arg Ser Asn
            20                  25                  30

<210> SEQ ID NO 31
<211> LENGTH: 24
<212> TYPE: PRT
<213> ORGANISM: Artificial Sequence
<220> FEATURE:
<223> OTHER INFORMATION: Peptide P7

<400> SEQUENCE: 31

Ala Asn Ile Ala Val Asp Lys Ala Asn Leu Glu Ile Met Thr Lys Arg
1               5                   10                  15

Ser Asn Tyr Thr Pro Ile Thr Asn
            20

<210> SEQ ID NO 32
<211> LENGTH: 21
<212> TYPE: PRT
<213> ORGANISM: Artificial Sequence
<220> FEATURE:
<223> OTHER INFORMATION: Human MOG-35-55

<400> SEQUENCE: 32

Met Glu Val Gly Trp Tyr Arg Pro Pro Phe Ser Arg Val Val His Leu
1               5                   10                  15

Tyr Arg Asn Gly Lys
            20

<210> SEQ ID NO 33
<211> LENGTH: 21
<212> TYPE: PRT
<213> ORGANISM: Artificial Sequence
<220> FEATURE:
<223> OTHER INFORMATION: Mouse MOG-35-55

<400> SEQUENCE: 33

Met Glu Val Gly Trp Tyr Arg Ser Pro Phe Ser Arg Val Val His Leu
1               5                   10                  15

Tyr Arg Asn Gly Lys
            20

<210> SEQ ID NO 34
<211> LENGTH: 15
<212> TYPE: PRT
<213> ORGANISM: Artificial Sequence
<220> FEATURE:
<223> OTHER INFORMATION: IRBP 1177-1191

<400> SEQUENCE: 34

Ala Asp Gly Ser Ser Trp Glu Gly Val Gly Val Val Pro Asp Val
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Arrestin 291-310

<400> SEQUENCE: 35

Asn Arg Glu Arg Arg Gly Ile Ala Leu Asp Gly Lys Ile Lys His Glu
1               5                   10                  15

Asp Thr Asn Leu
            20

<210> SEQ ID NO 36
<211> LENGTH: 32
<212> TYPE: PRT
<213> ORGANISM: Artificial Sequence
<220> FEATURE:
<223> OTHER INFORMATION: Phosducin 65-96

```
<400> SEQUENCE: 36

Lys Glu Arg Met Ser Arg Lys Met Ser Ile Gln Glu Tyr Glu Leu Ile
1               5                   10                  15

His Gln Asp Lys Glu Asp Glu Gly Cys Leu Arg Lys Tyr Arg Arg Gln
            20                  25                  30

<210> SEQ ID NO 37
<211> LENGTH: 5
<212> TYPE: PRT
<213> ORGANISM: Artificial Sequence
<220> FEATURE:
<223> OTHER INFORMATION: Recoverin 48-52

<400> SEQUENCE: 37

Gln Phe Gln Ser Ile
1               5

<210> SEQ ID NO 38
<211> LENGTH: 7
<212> TYPE: PRT
<213> ORGANISM: Artificial Sequence
<220> FEATURE:
<223> OTHER INFORMATION: Recoverin 64-70

<400> SEQUENCE: 38

Lys Ala Tyr Ala Gln His Val
1               5

<210> SEQ ID NO 39
<211> LENGTH: 20
<212> TYPE: PRT
<213> ORGANISM: Artificial Sequence
<220> FEATURE:
<223> OTHER INFORMATION: Recoverin 62-81

<400> SEQUENCE: 39

Pro Lys Ala Tyr Ala Gln His Val Phe Arg Ser Phe Asp Ala Asn Ser
1               5                   10                  15

Asp Gly Thr Leu
            20

<210> SEQ ID NO 40
<211> LENGTH: 14
<212> TYPE: PRT
<213> ORGANISM: Artificial Sequence
<220> FEATURE:
<223> OTHER INFORMATION: Recoverin 149-162

<400> SEQUENCE: 40

Glu Lys Arg Ala Glu Lys Ile Trp Ala Ser Phe Gly Lys Lys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Collagen II 261-274

<400> SEQUENCE: 41

Ala Gly Phe Lys Gly Glu Gln Gly Pro Lys Gly Glu Pro Gly
1               5                   10

<210> SEQ ID NO 42
```

```
<211> LENGTH: 15
<212> TYPE: PRT
<213> ORGANISM: Artificial Sequence
<220> FEATURE:
<223> OTHER INFORMATION: Collagen II 259-273

<400> SEQUENCE: 42

Gly Ile Ala Gly Phe Lys Gly Glu Gln Gly Pro Lys Gly Glu Pro
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Collagen II 257-270

<400> SEQUENCE: 43

Glu Pro Gly Ile Ala Gly Phe Lys Gly Glu Gln Gly Pro Lys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Modified collagen II257-270

<400> SEQUENCE: 44

Ala Pro Gly Ile Ala Gly Phe Lys Ala Glu Gln Ala Ala Lys
1               5                   10

<210> SEQ ID NO 45
<211> LENGTH: 20
<212> TYPE: PRT
<213> ORGANISM: Artificial Sequence
<220> FEATURE:
<223> OTHER INFORMATION: fibrinogen-alpha  40-59

<400> SEQUENCE: 45

Val Glu Arg His Gln Ser Ala Cys Lys Asp Ser Asp Trp Pro Phe Cys
1               5                   10                  15

Ser Asp Glu Asp
            20

<210> SEQ ID NO 46
<211> LENGTH: 20
<212> TYPE: PRT
<213> ORGANISM: Artificial Sequence
<220> FEATURE:
<223> OTHER INFORMATION: fibrinogen-alpha 616-625

<400> SEQUENCE: 46

Thr His Ser Thr Lys Arg Gly His Ala Lys Ser Arg Pro Val Arg Gly
1               5                   10                  15

Ile His Thr Ser
            20

<210> SEQ ID NO 47
<211> LENGTH: 13
<212> TYPE: PRT
<213> ORGANISM: Artificial Sequence
<220> FEATURE:
<223> OTHER INFORMATION: fibrinogen-alpha 79-91

<400> SEQUENCE: 47
```

-continued

Gln Asp Phe Thr Asn Arg Ile Asn Lys Leu Lys Asn Ser
1               5                   10

<210> SEQ ID NO 48
<211> LENGTH: 20
<212> TYPE: PRT
<213> ORGANISM: Artificial Sequence
<220> FEATURE:
<223> OTHER INFORMATION: fibrinogen-alpha 121-140

<400> SEQUENCE: 48

Asn Asn Arg Asp Asn Thr Tyr Asn Arg Val Ser Glu Asp Leu Arg Ser
1               5                   10                  15

Arg Ile Glu Val
            20

<210> SEQ ID NO 49
<211> LENGTH: 21
<212> TYPE: PRT
<213> ORGANISM: Artificial Sequence
<220> FEATURE:
<223> OTHER INFORMATION: vimentin 59-79

<400> SEQUENCE: 49

Gly Val Tyr Ala Thr Arg Ser Ser Ala Val Arg Leu Arg Ser Ser Val
1               5                   10                  15

Pro Gly Val Arg Leu
            20

<210> SEQ ID NO 50
<211> LENGTH: 19
<212> TYPE: PRT
<213> ORGANISM: Artificial Sequence
<220> FEATURE:
<223> OTHER INFORMATION: vinmentin 26-44

<400> SEQUENCE: 50

Ser Ser Arg Ser Tyr Val Thr Thr Ser Thr Arg Thr Tyr Ser Leu Gly
1               5                   10                  15

Ser Ala Leu

<210> SEQ ID NO 51
<211> LENGTH: 20
<212> TYPE: PRT
<213> ORGANISM: Artificial Sequence
<220> FEATURE:
<223> OTHER INFORMATION: vimentin 256-275

<400> SEQUENCE: 51

Ile Asp Val Asp Val Ser Lys Pro Asp Leu Thr Ala Ala Leu Arg Asp
1               5                   10                  15

Val Arg Gln Gln
            20

<210> SEQ ID NO 52
<211> LENGTH: 19
<212> TYPE: PRT
<213> ORGANISM: Artificial Sequence
<220> FEATURE:
<223> OTHER INFORMATION: vimentin 415-433

<400> SEQUENCE: 52

Leu Pro Asn Phe Ser Ser Leu Asn Leu Arg Glu Thr Asn Leu Asp Ser
1               5                   10                  15

Leu Pro Leu

```
<210> SEQ ID NO 53
<211> LENGTH: 17
<212> TYPE: PRT
<213> ORGANISM: Artificial Sequence
<220> FEATURE:
<223> OTHER INFORMATION: alpha-enolase 5-21

<400> SEQUENCE: 53
```

Lys Ile His Ala Arg Glu Ile Phe Asp Ser Arg Gly Asn Pro Thr Val
1               5                   10                  15

Glu

```
<210> SEQ ID NO 54
<211> LENGTH: 13
<212> TYPE: PRT
<213> ORGANISM: Artificial Sequence
<220> FEATURE:
<223> OTHER INFORMATION: human cartilege glycoprotein 39 259-271

<400> SEQUENCE: 54
```

Pro Thr Phe Gly Arg Ser Phe Thr Leu Ala Ser Ser Glu
1               5                   10

```
<210> SEQ ID NO 55
<211> LENGTH: 15
<212> TYPE: PRT
<213> ORGANISM: Artificial Sequence
<220> FEATURE:
<223> OTHER INFORMATION: myelin basic protein 85-99

<400> SEQUENCE: 55
```

Glu Asn Pro Val Val His Phe Phe Lys Asn Ile Val Thr Pro Arg
1               5                   10                  15

```
<210> SEQ ID NO 56
<211> LENGTH: 20
<212> TYPE: PRT
<213> ORGANISM: Artificial Sequence
<220> FEATURE:
<223> OTHER INFORMATION: myelin basic protein 145-164

<400> SEQUENCE: 56
```

Val Asp Ala Gln Gly Thr Leu Ser Lys Ile Phe Lys Leu Gly Gly Arg
1               5                   10                  15

Asp Ser Arg Ser
        20

```
<210> SEQ ID NO 57
<211> LENGTH: 16
<212> TYPE: PRT
<213> ORGANISM: Artificial Sequence
<220> FEATURE:
<223> OTHER INFORMATION: proteolipid protein 139-151

<400> SEQUENCE: 57
```

Cys His Cys Leu Gly Lys Trp Leu Gly His Pro Asp Lys Phe Val Gly
1               5                   10                  15

```
<210> SEQ ID NO 58
<211> LENGTH: 22
<212> TYPE: PRT
<213> ORGANISM: Artificial Sequence
<220> FEATURE:
<223> OTHER INFORMATION: proteolipid protein 95-116
```

```
<400> SEQUENCE: 58

Gly Ala Val Arg Gln Ile Phe Gly Asp Tyr Lys Thr Thr Ile Cys Gly
1               5                   10                  15

Lys Gly Leu Ser Ala Thr
            20

<210> SEQ ID NO 59
<211> LENGTH: 20
<212> TYPE: PRT
<213> ORGANISM: Artificial Sequence
<220> FEATURE:
<223> OTHER INFORMATION: MOG 1-25

<400> SEQUENCE: 59

Gly Gln Phe Arg Val Ile Gly Pro Arg His Pro Ile Arg Ala Leu Val
1               5                   10                  15

Gly Asp Glu Val
            20

<210> SEQ ID NO 60
<211> LENGTH: 23
<212> TYPE: PRT
<213> ORGANISM: Artificial Sequence
<220> FEATURE:
<223> OTHER INFORMATION: MOG 94-116

<400> SEQUENCE: 60

Gly Gly Phe Thr Cys Phe Phe Arg Asp His Ser Tyr Gln Glu Glu Ala
1               5                   10                  15

Ala Met Glu Leu Lys Val Glu
            20

<210> SEQ ID NO 61
<211> LENGTH: 16
<212> TYPE: PRT
<213> ORGANISM: Artificial Sequence
<220> FEATURE:
<223> OTHER INFORMATION: MOG 145-160

<400> SEQUENCE: 61

Val Phe Leu Cys Leu Gln Tyr Arg Leu Arg Gly Lys Leu Arg Ala Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: MOG 194-208

<400> SEQUENCE: 62

Leu Val Ala Leu Ile Ile Cys Tyr Asn Trp Leu His Arg Arg Leu
1               5                   10                  15

<210> SEQ ID NO 63
<211> LENGTH: 10
<212> TYPE: PRT
<213> ORGANISM: Artificial Sequence
<220> FEATURE:
<223> OTHER INFORMATION: alpha2-gliadin 61-71

<400> SEQUENCE: 63

Pro Gln Pro Glu Leu Pro Tyr Pro Gln Pro
1               5                   10
```

```
<210> SEQ ID NO 64
<211> LENGTH: 20
<212> TYPE: PRT
<213> ORGANISM: Artificial Sequence
<220> FEATURE:
<223> OTHER INFORMATION: alpha-2 gliadin 58-77

<400> SEQUENCE: 64

Leu Gln Pro Phe Pro Gln Pro Gln Leu Pro Tyr Pro Gln Pro Gln Leu
1               5                   10                  15

Pro Tyr Pro Gln
            20
```